United States Patent
Buckberry

(10) Patent No.: US 12,251,504 B2
(45) Date of Patent: Mar. 18, 2025

(54) DIALYSIS SYSTEMS, DEVICES AND METHODS

(71) Applicant: QUANTA DIALYSIS TECHNOLOGIES, LTD., Warwickshire (GB)

(72) Inventor: Clive Buckberry, Warwickshire (GB)

(73) Assignee: QUANTA DIALYSIS TECHNOLOGIES LTD., Warwickshire (GB)

(*) Notice: Subject to any disclaimer, the term of this patent is extended or adjusted under 35 U.S.C. 154(b) by 171 days.

(21) Appl. No.: 16/019,211

(22) Filed: Jun. 26, 2018

(65) Prior Publication Data

US 2019/0001042 A1    Jan. 3, 2019

(30) Foreign Application Priority Data

Jun. 30, 2017    (GB) ...................... 1710546

(51) Int. Cl.
*A61M 1/16*    (2006.01)
*A61M 1/14*    (2006.01)
(Continued)

(52) U.S. Cl.
CPC .......... *A61M 1/1672* (2014.02); *A61M 1/154* (2022.05); *A61M 1/155* (2022.05);
(Continued)

(58) Field of Classification Search
CPC .............. A61M 1/1672; A61M 1/1607; A61M 1/1635; A61M 1/1656; A61M 1/3413;
(Continued)

(56) References Cited

U.S. PATENT DOCUMENTS 2,696,173 A    12/1954    Thormod et al.
3,338,171 A    8/1967    Conklin et al.
(Continued)

FOREIGN PATENT DOCUMENTS

CA            81430 S    8/1997
DE        10024447 A1    11/2001
(Continued)

OTHER PUBLICATIONS

Kivi, Air Embolism, Aug. 20, 2012, p. 1-5 (Year: 2012).*
(Continued)

*Primary Examiner* — Dirk R Bass
(74) *Attorney, Agent, or Firm* — The Marbury Law Group, PLLC

(57) ABSTRACT

The disclosure relates to a dialysis system comprising a dialysate side and a blood side. In particular, and for example, in some embodiments, a dialysis system is provided and comprises a dialyzer including and a blood filter configured to divide the dialyzer and dialysis system into a blood side and a dialysate side. The blood side includes a blood circuit comprising a blood pump, a blood removal line, a blood return line, and a blood return line valve (BRV). The blood removal line and blood return line converge to a single venous access line in blood communication with a patient. The dialysate side includes a dialysate fluid circuit comprising first and second pump chambers each having a plurality of respective valves configurable to enable or prevent fluid communication with both the dialyser side of the dialyser and a drain. Each of the first and second pump chambers are configurable, based on the configurations of the valves, to comprise a blood accumulation chamber.

5 Claims, 9 Drawing Sheets

(51) Int. Cl.
*A61M 1/30* (2006.01)
*A61M 1/34* (2006.01)
*A61M 1/36* (2006.01)

(52) U.S. Cl.
CPC ...... *A61M 1/15625* (2022.05); *A61M 1/1565* (2022.05); *A61M 1/1601* (2014.02); *A61M 1/1635* (2014.02); *A61M 1/1656* (2013.01); *A61M 1/30* (2013.01); *A61M 1/3413* (2013.01); *A61M 1/3646* (2014.02); *A61M 1/365* (2014.02); *A61M 1/168* (2013.01); *A61M 2205/123* (2013.01); *A61M 2205/126* (2013.01); *A61M 2205/50* (2013.01)

(58) Field of Classification Search
CPC .... A61M 1/3646; A61M 1/365; A61M 1/168; A61M 2205/123; A61M 2205/126; A61M 2205/50; A61M 2205/128; A61M 1/16; A61M 1/1601; A61M 1/34; A61M 2202/0413; A61M 2205/12; A61M 2230/06; A61M 1/1696; A61M 1/30; A61M 1/342; A61M 1/3434; A61M 1/3441; A61M 2205/33; A61M 2205/3331; A61M 2230/005; A61M 1/1621; A61M 1/1645; A61M 1/1647; A61M 1/1649; A61M 1/166; A61M 1/1666; A61M 1/1668; A61M 1/1682; A61M 1/1686; A61M 1/169; A61M 1/267; A61M 1/28; A61M 1/303; A61M 1/3403; A61M 1/3417; A61M 1/3427; A61M 1/3437; A61M 1/3458; A61M 1/3465; A61M 1/3621; A61M 1/3635; A61M 1/3656; A61M 1/367; A61M 1/3672; A61M 1/3675; A61M 2205/121; A61M 2205/3306; A61M 2205/3313; A61M 2205/3317; A61M 2205/3324; A61M 2205/3327; A61M 2205/3334; A61M 2205/3368; A61M 2205/75; A61M 2205/7563; A61M 2209/00; A61M 2230/04; A61M 39/08; A61M 39/22; A61M 60/113; A61M 60/268; A61M 60/43; A61M 60/50; A61M 1/3482; A61M 2202/0021; A61M 1/154; A61M 1/155; A61M 1/1561; A61M 1/15625; A61M 1/1565; A61M 1/1524; A61M 1/14; A61M 1/1605; A61M 1/1609; A61M 1/1688; A61M 2205/15; A61M 2205/18; A61M 2205/273; A61M 2205/3375; A61M 2205/36; A61M 2205/3653; A61M 2205/581; A61M 2205/583; A61M 2205/702; A61M 60/37; A61M 60/427; A61M 60/562; A61M 60/837; A61M 60/847; A61M 60/849; A61M 60/851; F04B 43/026; F04B 2201/0605; F04B 51/00; Y10T 137/85938; A61L 2/04; A61L 2/24; A61L 2202/14; A61L 2202/22; C02F 1/008; C02F 1/02; C02F 2103/026; C02F 2209/005; C02F 2209/02; C02F 2209/44; C02F 2303/04

See application file for complete search history.

(56) References Cited

U.S. PATENT DOCUMENTS

| | | |
|---|---|---|
| 3,468,261 A | 9/1969 | Schmierer et al. |
| 3,605,566 A | 9/1971 | Vetter et al. |
| 3,606,592 A | 9/1971 | Madurski et al. |
| 3,753,493 A | 8/1973 | Mellor |
| 3,774,762 A | 11/1973 | Lichtenstein |
| 3,807,906 A | 4/1974 | Breit |
| 3,921,622 A | 11/1975 | Cole |
| 3,972,320 A | 8/1976 | Kalman |
| 4,070,725 A | 1/1978 | Austin et al. |
| 4,142,845 A | 3/1979 | Lepp et al. |
| 4,161,264 A | 7/1979 | Malmgren |
| 4,205,686 A | 6/1980 | Harris et al. |
| 4,353,990 A | 10/1982 | Manske et al. |
| 4,366,061 A | 12/1982 | Papanek et al. |
| 4,368,261 A | 1/1983 | Klose et al. |
| 4,370,983 A | 2/1983 | Lichtenstein |
| 4,430,048 A | 2/1984 | Fritsch |
| 4,494,912 A | 1/1985 | Pauliukonis |
| D277,991 S | 3/1985 | Becker |
| 4,534,755 A | 8/1985 | Calvert et al. |
| 4,534,756 A | 8/1985 | Nelson |
| 4,546,669 A | 10/1985 | Fischer et al. |
| 4,564,342 A | 1/1986 | Weber et al. |
| 4,599,165 A * | 7/1986 | Chevallet ............... A61M 1/30 210/257.2 |
| 4,648,869 A | 3/1987 | Bobo, Jr. |
| 4,666,598 A | 5/1987 | Heath et al. |
| 4,710,163 A | 12/1987 | Butterfield |
| 4,771,792 A | 9/1988 | Seale |
| 4,828,543 A | 5/1989 | Weiss et al. |
| 4,897,184 A | 1/1990 | Shouldice et al. |
| D308,249 S | 5/1990 | Buckley |
| 4,969,991 A | 11/1990 | Valadez |
| 5,000,664 A | 3/1991 | Lawless et al. |
| 5,012,197 A | 4/1991 | Seiffert et al. |
| 5,032,265 A | 7/1991 | Jha et al. |
| 5,055,198 A * | 10/1991 | Shettigar ............. A61M 1/3403 210/650 |
| 5,095,910 A | 3/1992 | Powers |
| 5,103,211 A | 4/1992 | Daoud et al. |
| 5,126,831 A | 6/1992 | Nakagawara |
| 5,232,434 A | 8/1993 | Inagaki et al. |
| 5,252,213 A | 10/1993 | Ahmad et al. |
| D341,890 S | 11/1993 | Sievert et al. |
| D344,339 S | 2/1994 | Yoshikawa et al. |
| 5,304,349 A | 4/1994 | Polaschegg |
| D347,896 S | 6/1994 | Dickinson et al. |
| D351,470 S | 10/1994 | Scherer et al. |
| 5,385,540 A | 1/1995 | Abbott et al. |
| 5,421,823 A | 6/1995 | Kamen et al. |
| 5,458,468 A | 10/1995 | Ye et al. |
| 5,476,368 A | 12/1995 | Rabenau et al. |
| 5,476,792 A | 12/1995 | Ezrielev et al. |
| D370,979 S | 6/1996 | Pascale et al. |
| 5,558,347 A | 9/1996 | Nicholson |
| 5,586,872 A | 12/1996 | Skobelev et al. |
| 5,586,873 A | 12/1996 | Novak et al. |
| 5,591,344 A | 1/1997 | Kenley et al. |
| 5,643,201 A | 7/1997 | Peabody et al. |
| 5,650,071 A | 7/1997 | Brugger et al. |
| 5,653,456 A | 8/1997 | Mough |
| 5,658,456 A | 8/1997 | Kenley et al. |
| 5,665,307 A | 9/1997 | Kirschner et al. |
| 5,727,550 A | 3/1998 | Montecalvo |
| D395,085 S | 6/1998 | Kenley et al. |
| 5,788,851 A | 8/1998 | Kenley et al. |
| 5,807,322 A | 9/1998 | Lindsey et al. |
| 5,882,300 A | 3/1999 | Malinouskas et al. |
| 5,948,247 A | 9/1999 | Gillerfalk et al. |
| 5,957,670 A | 9/1999 | Duncan et al. |
| 5,995,910 A | 11/1999 | Discenzo |
| 6,077,443 A | 6/2000 | Goldau |
| 6,126,831 A | 10/2000 | Goldau et al. |
| 6,132,378 A | 10/2000 | Marino |
| 6,143,181 A | 11/2000 | Falkvall et al. |
| 6,153,102 A | 11/2000 | Kenley et al. |
| 6,216,029 B1 | 4/2001 | Paltieli |
| 6,218,329 B1 | 4/2001 | Singh et al. |
| 6,251,279 B1 | 6/2001 | Peterson et al. |
| 6,261,065 B1 | 7/2001 | Nayak et al. |
| 6,303,036 B1 | 10/2001 | Collins et al. |

(56) References Cited

U.S. PATENT DOCUMENTS

| | | |
|---|---|---|
| 6,382,923 B1 | 5/2002 | Gray |
| 6,514,462 B1 | 2/2003 | Simons |
| 6,558,347 B1 | 5/2003 | Jhuboo et al. |
| 6,582,206 B2 | 6/2003 | Schluecker |
| 6,626,832 B1 | 9/2003 | Paltieli et al. |
| 6,626,878 B1 | 9/2003 | Leisner et al. |
| 6,645,176 B1 | 11/2003 | Christenson et al. |
| 6,663,829 B1 | 12/2003 | Kjellstrand |
| 6,733,476 B2 | 5/2004 | Christenson et al. |
| 6,743,204 B2 | 6/2004 | Christenson et al. |
| 6,801,646 B1 | 10/2004 | Pena et al. |
| 6,814,547 B2 | 11/2004 | Childers et al. |
| 6,967,002 B1 | 11/2005 | Edgson et al. |
| 7,040,142 B2 | 5/2006 | Burbank |
| 7,107,837 B2 | 9/2006 | Lauman et al. |
| 7,153,286 B2 | 12/2006 | Busby et al. |
| 7,284,964 B2 | 10/2007 | McDowell et al. |
| 7,434,312 B2 | 10/2008 | Christenson et al. |
| 7,494,590 B2 | 2/2009 | Felding et al. |
| 7,648,627 B2 | 1/2010 | Beden et al. |
| 7,857,976 B2 | 12/2010 | Bissler et al. |
| 7,874,999 B2 | 1/2011 | Busby |
| 7,896,197 B2 | 3/2011 | Furey et al. |
| D641,882 S | 7/2011 | Hickey et al. |
| 8,114,043 B2 | 2/2012 | Muller |
| 8,132,388 B2 | 3/2012 | Nagy et al. |
| 8,137,184 B2 | 3/2012 | Ajiro et al. |
| 8,137,300 B2 | 3/2012 | Han et al. |
| 8,167,431 B2 | 5/2012 | DeCusatis et al. |
| 8,187,184 B2 | 5/2012 | Muller et al. |
| 8,192,388 B2 | 6/2012 | Hogard |
| 8,197,431 B2 | 6/2012 | Bennison |
| 8,221,320 B2 | 7/2012 | Bouton |
| 8,348,850 B2 | 1/2013 | Frinak et al. |
| 8,360,977 B2 | 1/2013 | Marttila et al. |
| 8,529,490 B2 | 9/2013 | Wariar et al. |
| 8,535,522 B2 | 9/2013 | Fulkerson et al. |
| 8,535,525 B2 | 9/2013 | Heyes et al. |
| D693,469 S | 11/2013 | Chung et al. |
| 8,597,505 B2 | 12/2013 | Fulkerson et al. |
| D702,842 S | 4/2014 | Hyde et al. |
| 8,685,244 B2 | 4/2014 | Heyes et al. |
| 8,696,571 B2 | 4/2014 | Marttila et al. |
| 8,708,908 B2 | 4/2014 | Bouton |
| 8,708,946 B2 | 4/2014 | Han et al. |
| D705,432 S | 5/2014 | Lura et al. |
| 8,798,908 B2 | 8/2014 | Bourdeaut |
| 8,801,646 B2 | 8/2014 | Han et al. |
| D714,454 S | 9/2014 | Amemiya et al. |
| D714,946 S | 10/2014 | Lura et al. |
| 8,926,544 B2 | 1/2015 | Hogard |
| D724,740 S | 3/2015 | Collins et al. |
| 8,974,394 B2 | 3/2015 | Frinak et al. |
| 9,011,334 B2 | 4/2015 | Bouton |
| D735,868 S | 8/2015 | Mareguddi et al. |
| 9,220,825 B2 | 12/2015 | Buckberry |
| D781,410 S | 3/2017 | Ritter et al. |
| 9,744,285 B2 | 8/2017 | Heyes et al. |
| 9,833,553 B2 | 12/2017 | Higgitt et al. |
| 10,456,516 B2 | 10/2019 | Heyes et al. |
| D867,597 S | 11/2019 | Bauer et al. |
| 10,543,305 B2 | 1/2020 | Buckberry et al. |
| D879,967 S | 3/2020 | Verguldi et al. |
| D907,211 S | 1/2021 | Spurling |
| 10,881,775 B2 | 1/2021 | Wallace |
| 10,960,120 B2 | 3/2021 | Wallace et al. |
| D924,410 S | 7/2021 | Mendoza et al. |
| D938,046 S | 12/2021 | Gupta et al. |
| 11,365,728 B2 | 6/2022 | Westenbrink |
| 2003/0217962 A1 | 11/2003 | Childers et al. |
| 2004/0195157 A1 | 10/2004 | Mullins et al. |
| 2004/0206703 A1 | 10/2004 | Bosetto et al. |
| 2004/0215129 A1 | 10/2004 | Edgson et al. |
| 2004/0223857 A1 | 11/2004 | Kline |
| 2005/0020961 A1 | 1/2005 | Burbank et al. |
| 2005/0205476 A1* | 9/2005 | Chevallet ............... A61M 1/303 210/85 |
| 2005/0209547 A1 | 9/2005 | Burbank et al. |
| 2005/0234384 A1 | 10/2005 | Westberg |
| 2006/0121623 A1 | 6/2006 | He et al. |
| 2007/0083193 A1 | 4/2007 | Werneth et al. |
| 2008/0200865 A1 | 8/2008 | Bedingfield |
| 2008/0283096 A1 | 11/2008 | Scheringer et al. |
| 2009/0007642 A1 | 1/2009 | Busby et al. |
| 2009/0009290 A1 | 1/2009 | Kneip et al. |
| 2009/0012450 A1 | 1/2009 | Shah et al. |
| 2009/0012452 A1 | 1/2009 | Slepicka et al. |
| 2009/0012457 A1 | 1/2009 | Childers et al. |
| 2009/0101550 A1 | 4/2009 | Muller et al. |
| 2009/0211975 A1 | 8/2009 | Brugger et al. |
| 2009/0230043 A1 | 9/2009 | Heyes et al. |
| 2010/0043694 A1 | 2/2010 | Patel |
| 2010/0045471 A1 | 2/2010 | Meyers |
| 2010/0089807 A1 | 4/2010 | Heyes et al. |
| 2010/0139254 A1 | 6/2010 | Sebestyen et al. |
| 2010/0263687 A1 | 10/2010 | Braun et al. |
| 2011/0009797 A1 | 1/2011 | Kelly et al. |
| 2011/0034850 A1* | 2/2011 | Jonsson ............... A61M 1/303 604/4.01 |
| 2011/0132838 A1 | 6/2011 | Curtis et al. |
| 2011/0168614 A1* | 7/2011 | Pouchoulin ......... A61M 1/3437 210/134 |
| 2012/0164022 A1 | 6/2012 | Muginstein et al. |
| 2012/0269907 A1 | 10/2012 | Coates |
| 2012/0276549 A1 | 11/2012 | Cunningham et al. |
| 2012/0292237 A1 | 11/2012 | Heyes et al. |
| 2012/0308431 A1 | 12/2012 | Kotsos et al. |
| 2013/0056419 A1 | 3/2013 | Curtis |
| 2013/0153495 A1 | 6/2013 | Kelly et al. |
| 2013/0199998 A1* | 8/2013 | Kelly ............... A61M 1/1696 210/646 |
| 2013/0274642 A1 | 10/2013 | Soykan et al. |
| 2014/0224736 A1* | 8/2014 | Heide ............... A61M 1/1647 210/646 |
| 2014/0251885 A1 | 9/2014 | Heyes |
| 2014/0299544 A1 | 10/2014 | Wilt et al. |
| 2015/0027951 A1 | 1/2015 | Wallace et al. |
| 2015/0076053 A1 | 3/2015 | Higgitt et al. |
| 2015/0112119 A1 | 4/2015 | Buckberry |
| 2015/0129481 A1 | 5/2015 | Higgitt et al. |
| 2015/0238673 A1 | 8/2015 | Gerber et al. |
| 2015/0258263 A1 | 9/2015 | Hogard |
| 2015/0352269 A1 | 12/2015 | Gerber et al. |
| 2015/0359954 A1 | 12/2015 | Gerber et al. |
| 2016/0045656 A1* | 2/2016 | Buckberry ............ A61M 1/166 210/91 |
| 2016/0051743 A1* | 2/2016 | Buckberry ............ A61M 1/16 210/636 |
| 2016/0058933 A1 | 3/2016 | Ballantyne et al. |
| 2016/0077644 A1 | 3/2016 | Ritter et al. |
| 2017/0056576 A1 | 3/2017 | Doyle et al. |
| 2017/0167983 A1 | 6/2017 | Klomp et al. |
| 2017/0252498 A1 | 9/2017 | Heyes et al. |
| 2017/0296730 A1 | 10/2017 | Soto et al. |
| 2018/0133391 A1 | 5/2018 | Heyes et al. |
| 2018/0154059 A1 | 6/2018 | Heyes et al. |
| 2018/0193545 A1 | 7/2018 | Crnkovich et al. |
| 2018/0344915 A1 | 12/2018 | Wallace |
| 2019/0015577 A1 | 1/2019 | Garrido et al. |
| 2019/0024654 A1 | 1/2019 | May et al. |
| 2019/0358381 A1 | 11/2019 | Westenbrink |
| 2019/0374698 A1 | 12/2019 | Buckberry et al. |
| 2019/0376504 A1 | 12/2019 | Westenbrink |
| 2019/0385434 A1 | 12/2019 | Yuds et al. |
| 2020/0030515 A1 | 1/2020 | Merchant |
| 2020/0075159 A1 | 3/2020 | Bardorz et al. |
| 2020/0268958 A1 | 8/2020 | Heyes et al. |
| 2020/0276372 A1 | 9/2020 | Milad et al. |
| 2020/0330671 A1 | 10/2020 | Buckberry et al. |

(56) References Cited

U.S. PATENT DOCUMENTS

| | | | |
|---|---|---|---|
| 2022/0001087 A1 | 1/2022 | Heyes et al. | |
| 2022/0160943 A9 | 5/2022 | Buckberry et al. | |

FOREIGN PATENT DOCUMENTS

| | | |
|---|---|---|
| EM | EU0043757640001 | 10/2017 |
| EM | EU0043757640002 | 10/2017 |
| EM | EU0079551250002 | 6/2020 |
| EP | 0165751 A2 | 12/1985 |
| EP | 0754468 A2 | 1/1997 |
| EP | 2219703 A1 | 8/2010 |
| EP | 2955512 A1 | 12/2015 |
| FR | 2310136 A1 | 12/1976 |
| GB | 90079551250001 | 5/2020 |
| GB | 90079551250002 | 5/2020 |
| JP | H04266740 | 9/1992 |
| JP | H06261872 | 9/1994 |
| JP | H07174659 A | 7/1995 |
| JP | 2000/130334 | 5/2000 |
| JP | 1645323 S | 11/2020 |
| WO | WO 81/01800 | 7/1981 |
| WO | WO-9100113 A2 | 1/1991 |
| WO | WO-9116542 A1 | 10/1991 |
| WO | WO 95/06205 | 3/1995 |
| WO | WO 95/25893 | 9/1995 |
| WO | WO-9625214 A1 | 8/1996 |
| WO | WO-9710013 A1 | 3/1997 |
| WO | WO-9728368 A2 | 8/1997 |
| WO | WO-9929356 A1 | 6/1999 |
| WO | WO 2000/006217 | 2/2000 |
| WO | WO-0057935 A1 | 10/2000 |
| WO | WO-02066833 A1 | 8/2002 |
| WO | WO-02081917 A1 | 10/2002 |
| WO | WO 2003/101510 | 12/2003 |
| WO | WO-2005044339 A2 | 5/2005 |
| WO | WO-2005080794 A1 | 9/2005 |
| WO | WO 2006/120415 | 11/2006 |
| WO | WO 2006/120417 | 11/2006 |
| WO | WO-2008100671 A1 | 8/2008 |
| WO | WO-2008106191 A2 | 9/2008 |
| WO | WO-2008135245 A1 | 11/2008 |
| WO | WO-2009006489 A1 | 1/2009 |
| WO | WO-2009024333 A1 | 2/2009 |
| WO | WO-2009038834 A1 | 3/2009 |
| WO | WO 2009/061608 | 5/2009 |
| WO | WO-2009127624 A2 | 10/2009 |
| WO | WO-2010089130 A1 | 8/2010 |
| WO | WO-2010146343 A2 | 12/2010 |
| WO | WO-2011027118 A1 | 3/2011 |
| WO | WO-2011068885 A1 | 6/2011 |
| WO | WO-2011105697 A2 | 9/2011 |
| WO | WO-2011105698 A2 | 9/2011 |
| WO | WO 2013/057109 | 4/2013 |
| WO | WO-2013052680 A2 | 4/2013 |
| WO | WO 2013/110906 | 8/2013 |
| WO | WO 2013/110919 | 8/2013 |
| WO | WO 2013/114063 | 8/2013 |
| WO | WO 2013/121162 | 8/2013 |
| WO | WO-2013121163 A1 | 8/2013 |
| WO | WO 2014/072195 | 5/2014 |
| WO | WO-2014082855 A1 | 6/2014 |
| WO | 2015022537 A1 | 8/2014 |
| WO | WO 2014/155121 | 10/2014 |
| WO | WO 2015/007596 | 1/2015 |
| WO | 2016016870 A2 | 2/2016 |
| WO | WO-2017137723 A1 | 8/2017 |
| WO | WO-2018115816 A1 | 6/2018 |

OTHER PUBLICATIONS

Search Report for Application No. GB1710546.1, mailed Dec. 22, 2017.

He et al., "A Fluorescent Sensor with High Selectivity and Sensitivity for Potassium in Water," Journal of the American Chemical Society 2003 125 (6), 1468-1469.

Ergo-Express Motorized Dialysis Cart, Aug. 14, 2017, youtube.com [online], Available from internet, URL: https:/ /www.youtube.com/watch?v=j4rAXthOmbY (Year: 2017).

Home Dialysis Tescon Aqua Tech, Aug. 1, 2020, youtube.com [online], Available from internet, URL: https:// www.youtube.com/watch?v=WLLPZoS_mz4 (Year: 2020).

LHO2028 Portable Hemodialysis Machine, date unknown, aliexpress.com [online], Available from internet: https ://www.aliexpress.com/item/1005003324875329.html?randl_currency=USD&_randl_shipto=US&src=google&afffcid=1003bab3b8db4e93b9ba88522a14cfc1-1641319351626-05232-UneMJZVf&aff_fsk=UneMJZVf&aff_platform=aaf&sk=UneMJZVf&aff_trace_key= (Year: 2022).

Medical Hemodialysis Machine, date unknown, aliexpress.com [online], Available from internet: https://www.aliexpress.com/item/1005003445721549.html ?_randl_currency=USD&_randl_shipto=US&src=google&aff_fcid=a524f3f9cd9b4976b6b47962f3439d62-1641319166409-02691-UneMJZVf&aff_fsk=UneMJZVf&aff_platform=aaf&sk=UneMJZVf&aff_trace_key=a524f3f9cd9b4976b6b47962f3439d62-1641319166409-02691-UneMJZVf&terminal_id=d0c2cca4b7664d 128cb4801 a9ef03ff2 (Year: 2022).

Millenium HX Portable Dialysis Water System, Jul. 2, 2014, youtube.com [online], Available from internet, URL: https://www.youtube.com/watch?v=IGEbPi2CDsw (Year: 2014).

Portable home dialysis device, Nov. 2, 2017, med-technews.com [online], Available from internet: https:// www.med-technews.com/news/portable-home-dialysis-device-to-launch-next-year/ (Year: 2017).

* cited by examiner

DIALYSIS SYSTEMS, DEVICES AND METHODS

FIELD OF DISCLOSURE

This application claims priority to GB1710546.1 filed Jun. 30, 2017, the entire disclosure of which is incorporated herein by reference. The disclosure relates to a dialysis system and method of operating the system. In particular, and according to some embodiments, the disclosure is directed to a system and method of operation which enables single-needle patient access.

BACKGROUND TO THE DISCLOSURE

Patients suffering from kidney disorders rely on a variety of external blood treatments to remove the harmful waste substances that build up in their blood over time. One of the most common methods of treatment is haemodialysis.

Haemodialysis typically involves two networks of fluid passageways running adjacent to one another in a counter current flow arrangement. Blood is passed through one set of tubules and a cleaning solution is passed through the other. The pH and osmotic potential of the cleaning solution is adapted such that waste compounds built up in the blood diffuse from the blood into the cleaning solution via a semi permeable membrane which separates the blood and cleaning solution sides of the network of fluid passageways.

This provides a method of gradually removing waste materials from the blood, minimising fatigue to the patient. However, there are some disadvantages associated with haemodialysis not present with other forms of blood treatment.

Many mid-size and large-size waste solutes dissolved in the blood (including such as proteins and polypeptides) are difficult to remove completely from the blood using diffusion alone and it can take a long time to reduce the levels of these substances in the blood to acceptable levels. An alternative approach is to use haemodiafiltration.

Haemodiafiltration involves administering sterile cleaning solution to the blood either by employing a large hydrostatic potential to force sterile cleaning solution across a semi permeable membrane into the blood or by directly adding it to the blood; and then pulling the sterile cleaning solution, complete with dissolved waste products, back across the semi permeable membrane for subsequent disposal. Examples of haemodiafiltration machines are disclosed in, for example "Lee, K., et al., *Evaluation of a New Method for Pulse Push/Pull Hemodialysis: Comparison with Conventional Hemodialysis*, ASAIO Journal, 2012, page 232-237". This type of blood treatment is not limited by diffusion as sterile cleaning solution is allowed to mix directly with the blood. However, the rapid extraction of waste products from a patient's blood regularly leaves patients fatigued as a consequence of changes in blood pressure due to the addition of substitution fluid to the blood.

In both methods, it is conventional to take blood from a patient's artery via a cannula into an arterial line, then a pump and into the dialyser cartridge. Treated blood then leaves the cartridge via a venous line and passes back to the patient's vein by a venous cannula. However, it is also known to use a single venous access for removal from, and return to, the body, of blood for treatment. When using a single venous access removal and return of blood must be done sequentially.

Single venous access may mitigate the possibility of exsanguination due to undetected venous needle dislodgement and is therefore seen as a desirable means of dialysing nocturnally. Three methods of single needle dialysis are known in the prior art. The first uses two peristaltic pump that exchange a volume of blood between them. The second utilizes a single peristaltic pump displacing blood to an accumulator located in the extracorporeal circuit. In a single peristaltic pump system, the accumulator stores the removed blood while the system is switched over to allow blood to be returned to the patient. Those methods are described by Polaschegg, in Haemodialysis Machines and Monitors, Replacement of Renal Function by Dialysis Handbook, page 365 to 368. Both methods are known to be more complex and require different tube sets from those used with dual needle access. In addition, the exchange of molecules across the dialyser is driven by diffusion. The third method is to use a single, dual lumen needle but this is subject to potential high recirculation between the two lumens of the single needle.

SUMMARY OF SOME OF THE EMBODIMENTS

It is an object of some of the embodiments of the disclosure to provide an improved dialysis system, which, according to some embodiments, is configured to effect a single-needle venous access.

In some embodiments, a dialysis system is provided and includes a dialysate fluid circuit, a blood circuit comprising a blood pump and a blood accumulator chamber, a dialyser comprising a fluid chamber, a dialysate inlet, a dialysate outlet, a blood inlet, and a blood outlet, and a blood filter arranged within the fluid chamber and configured to divide the system into a blood side and a dialysate side. The dialysate fluid circuit and the blood accumulator chamber are arranged on the dialysate side of the system.

The blood accumulator can be configured, in some embodiments, so as to enable a system and method for single needle venous access. This can be accomplished by arranging a blood accumulator chamber on a dialysate side of the system, while passing blood across the dialyser filter to reach the blood accumulator which mimics the action of hemodiafiltration (HDF) described above (only in reverse). In this way, no substitution fluid is required unlike in classic HDF. The forced movement of liquid across the dialyser creates solute drag of molecules normally too large to diffuse easily across the dialyser membrane.

In some embodiments, the dialysate output pump chamber comprises the blood accumulator chamber, which allows the dialysate output pump to return the blood to the patient.

Such embodiments (as noted above) may include one and/or another of the following structure, features, functionality and/or clarifications, thus yielding further embodiments:

the dialysate fluid circuit comprises a dialysate input pump having a dialysate input pump chamber, and/or a dialysate output pump having a dialysate output pump chamber;

the dialysate output pump chamber comprises the blood accumulator chamber;

the dialysate input pump chamber includes a dialysate inlet valve in fluid communication with a source of dialysate, and/or a dialysate outlet valve in fluid communication with the dialysate inlet of the dialyser;

the dialysate output pump chamber includes a spent dialysate inlet valve in fluid communication with the dialysate outlet of the dialyser, and/or a spent dialysate outlet valve in fluid communication with a drain;

the blood circuit further comprises a blood inlet line
upstream of the dialyser, a blood return line downstream of the dialyser, and/or a blood return line valve
arranged on the blood return line or at the blood outlet
of the dialyser;

a controller;

the dialysate fluid circuit comprises:

a first pump having a first pump chamber including a
fresh dialysate inlet valve in fluid communication
with a source of dialysate, a dialyser fluid line valve
in fluid communication with dialyser, and a drain
line valve in fluid communication with a drain; and a second pump having a second pump chamber with a
fresh dialysate inlet valve in fluid communication
with a source of dialysate, a dialyser fluid line valve
in fluid communication with a dialyser, and a drain
line valve in fluid communication with a drain;

a controller configured to control a plurality of the valves
(e.g., see above) such that one of the first pump and
second pump operates as the dialysate input pump, and
the remaining pump operates as the dialysate output
pump;

a controller configured to close off a respective drain
valve to effect operation of a respective pump as a
dialysate input pump;

a controller configured to close off a respective fresh
dialysate inlet valve to effect operation of a respective
pump as a dialysate output pump;

a controller configured to close off a respective drain
valve and a respective fresh dialysate inlet valve such
that the respective pump chamber of the respective
pump is configured to operate as the blood accumulator
chamber;

the dialysate fluid circuit comprises a body defining the
pump chambers closed by a membrane actuable to
effect pumping;

the body and membrane (see above) form a cartridge
configured for use with a dialysis apparatus which
includes actuators to actuate the membrane to effect
pumping, and the body can include a plurality of valves
which are configured to open and close by actuation of
the membrane;

the cartridge (see above) includes at least one mixing
chamber configured to effect mixing of dialysate constituents into a mixed dialysate; and the mixing chamber (see above) is in fluid communication
with the dialysate input pump.

As noted, the dialysate input and output pumps can be
membrane pumps, which can be a chamber adapted to hold
a volume of solution and a membrane sealing the chamber.
The membrane is configured to be forced down into the
chamber to expel the solution from the chamber. Thus, the
membrane can be a flexible membrane and can be fabricated
from an elastic material (for example), including a plastic or
polymeric material which can be configured to form a film
sealing one end of the chamber. In some embodiments, the
membrane can be extended to cover more than one chamber,
and in some embodiments, all the chambers (alternatively,
each membrane pump may include a separate membrane in
communication with a respective chamber).

Pumps can be arranged to pump a predetermined volume
of dialysate, and in some embodiments, are adapted to pump
the same volume of dialysate as each another pump. For
example, positive displacement pumps are adapted to pump
the same volume of solution as each other in each single
stroke. This ensures that the amount of solution pumped into
the dialyser by the first pump is the same as the amount of
solution drawn from the dialyser by the second pump.

In some embodiments, the dialysate input pump and
dialysate output pump are both operable either to deliver a
volume of dialysate from a dialysate source to the dialyser
or remove a volume of dialysate from the dialyser and
deliver said dialysate to a drain. Adapting both pumps to
function in this way allows the roles of each pump to be
periodically swapped (according to some embodiments).
This can be done at regular intervals in order to negate any
manufacturing discrepancies in the volume of the pump
chambers.

Pumps, according to some embodiments, an in particular,
dialysate pumps, can be formed as a disposable cartridge.
Moreover, in further embodiments, such cartridges can be
configured with additional structure and functionality
including valves and/or fluid passageways.

In some embodiments, a method of operating a dialysis
system is provided and includes one or more of (and in some
embodiments, a plurality of, and in still other embodiments
all of) the following steps:

(a) providing the dialysis system according to one or
another of the dialysis system embodiments disclosed
herein;

(b) providing a source of dialysate fluid, (c) connecting the vascular system of a patient to the
blood circuit, (d) supplying the dialysate fluid to the dialysate circuit
and supplying the blood to the blood circuit, (e) operating the dialysate outlet pump to draw blood
and/or operating the blood pump to push blood across
the blood filter onto the dialysate side and into the
dialysate outlet pump chamber, and (f) deactivating the blood pump and operating the
dialysate outlet pump so as to push blood back across
the blood filter into the blood side of the system.

Such embodiments may include one and/or another of the
following additional steps, structure, features, functionality
and/or clarifications, thus yielding further embodiments:

step (e) can include a first step (e1) which can comprising
one and/or another of the following:
deactivating the blood pump,
closing the blood return line so as to prevent the flow
of blood from the dialyser to the blood return line,
filling the dialysate input pump chamber with dialysate,
opening the dialysate outlet valve of the dialysate input
pump chamber,
emptying the dialysate output pump chamber,
opening the spent dialysate inlet valve,
closing the spent dialysate outlet valve,
actuating the dialysate input pump so as to push fresh
dialysate from the dialysate input pump chamber to
the dialyser, while simultaneously actuating the
dialysate output pump so as to draw spent dialysate
from the dialyser into the dialysate output pump
chamber, step (e) can include a second step (e2) comprising one
and/or another of the following:
deactivating the blood pump,
closing the blood return line,
emptying the dialysate input pump chamber,
filling the dialysate output pump chamber with spent
dialysate,
opening the dialysate inlet valve of the dialysate input
pump,
closing dialysate outlet valve of the dialysate input
pump, closing the spent dialysate inlet valve of the dialysate output pump, opening spent dialysate output valve of the dialysate output pump, and activating dialysate input pump so as to flow fresh dialysate from the dialysate source into the dialysate input pump chamber while simultaneously activating the dialysate output pump to push spent dialysate to drain.

In some embodiments, a method of testing a dialysis system is provided and includes one or more of (and in some embodiments, a plurality of, and in still other embodiments all of) the following steps:

(a) providing the dialysis system according to one or another of the dialysis system embodiments disclosed herein;

(b) providing a source of dialysate fluid;

(c) providing a source of blood analogue fluid;

(d) supplying the dialysate fluid to the dialysate circuit and supplying the blood analogue fluid to the blood circuit;

(e) at least one of operating the dialysate outlet pump to draw blood analogue fluid and operating the blood pump to push blood analogue fluid across the blood filter onto the dialysate side and into the dialysate outlet pump chamber; and (f) deactivating the blood pump and operating the dialysate outlet pump to push blood analogue fluid back across the blood filter onto the blood side of the system;

The blood analogue fluid can be a fluid designed to behave in a similar fashion to blood to enable the device to be tested, and can be, for example, blood plasma. The blood analogue fluid preferably includes a marker, such as a dye or a marker molecule, which may be sensed using appropriate sensors (e.g., Dextran tagged with fluoroscein for detection in a fluorometer).

The above-noted testing embodiments may include one and/or another of the following additional steps, structure, features, functionality and/or clarifications, thus yielding further embodiments:

step (e) may include a first step (e1) comprising:
deactivating the blood pump,
closing the blood return line valve,
filling the dialysate input pump chamber with dialysate,
opening the dialysate outlet valve of the dialysate input pump chamber,
emptying the dialysate output pump chamber,
opening the spent dialysate inlet valve,
closing the spent dialysate outlet valve, and
actuating the dialysate input pump so as to push fresh dialysate from the dialysate input pump chamber to the dialyser while simultaneously actuating the dialysate output pump to draw spent dialysate from the dialyser into the dialysate output pump chamber, step (e) includes a second step (e2) comprising:
deactivating the blood pump,
closing the blood return line,
emptying the dialysate input pump chamber,
filling the dialysate output pump chamber with spent dialysate,
opening the dialysate inlet valve of the dialysate input pump,
closing dialysate outlet valve of the dialysate input pump,
closing spent dialysate inlet valve of the dialysate output pump,
opening the spent dialysate output valve of the dialysate output pump, and
activating dialysate input pump so as to flow fresh dialysate from the dialysate source into the dialysate input pump chamber while simultaneously activating the dialysate output pump to push spent dialysate to drain.

In some embodiments, a dialysis system is provided and comprises a dialyzer including and a blood filter configured to divide the dialyzer and dialysis system into a blood side and a dialysate side. The blood side includes a blood circuit comprising a blood pump, a blood removal line, a blood return line, and a blood return line valve (BRV). The blood removal line and blood return line converge to a single venous access line in blood communication with a patient. The dialysate side includes a dialysate fluid circuit comprising first and second pump chambers each having a plurality of respective valves configurable to enable or prevent fluid communication with both the dialyser side of the dialyser and a drain. Each of the first and second pump chambers are configurable, based on the configurations of the valves, to comprise a blood accumulation chamber.

In some embodiments, a dialysis method is provided and comprises pumping spent dialysate solution contained in a dialyser into a first pump chamber of a dialysis system, pumping clean dialysate solution from a second pump chamber of the dialysis system to a dialysate side of a dialyser of the dialysis system, pumping the spent dialysate contained in the first pump chamber to a drain of the dialysis system, pumping clean dialysate fluid to the second pump chamber, such that thereafter:

pressurizing blood in a blood side of the dialyser relative to the dialysate side such that:
at least a portion of the blood plasma component of the blood contained in the blood side of the dialyser is forced across the blood filter to the dialysate side and mixes with dialysate solution contained therein,
the mixing of the at least a portion of the blood plasma component with the clean dialysate solution results in the production of spent dialysate solution, and
the spent dialysate solution is forced from the dialysate side into the first pump chamber;

pumping the spent dialysate solution from the first pump chamber into the dialysate side of the dialyser, whereby the portion of the blood plasma component contained in the spent dialysate solution passes back across the blood filter to the blood side of the dialyser, and pumping blood from the blood side of the dialyser back to the patient via a venous access line.

In some embodiments, a dialysis operational method is provided and comprises providing a dialysis system according to one and/or another of the dialysis system embodiments disclosed herein, and establishing a first condition in which the blood pump is inactive, the blood return valve is closed, the first pump chamber is empty, the second pump chamber contains clean dialysate solution, the blood side of the dialyser contains blood, and the dialysate side of the dialyser contains spent dialysate comprising a mixture of previously clean dialysate solution and at least a portion of blood plasma received from across the blood filter from blood contained in the blood side. The method also includes configuring of one or more of a plurality of valves (associated with the system) in a first configuration so as to enable the spent dialysate solution from the dialyser to be pumped or otherwise fluid communicated into the first pump chamber, pumping the spent dialysate solution from the dialyser into the first pump chamber, pumping clean dialysate solution from the second pump chamber to the dialysate side of the dialyser, configuring of one or more of the plurality of valves in a second configuration so as to enable the spent dialysate contained in the first pump chamber to be pumped or otherwise fluid communicated to a drain, and clean dialysate fluid to be pumped or otherwise fluid communicated to the second pump chamber, pumping the spent dialysate contained in the first pump chamber to the drain, pumping clean dialysate fluid to the second pump chamber, such that thereafter:

the first pump chamber is empty,
the second pump chamber is filled with clean dialysate solution,
the dialysate side of the dialyser is filled with clean dialysate fluid; and
the blood side of the is filled with blood.

The method may also include configuring of one or more of the plurality of valves in a third configuration, pressurizing the blood in the blood circuit relative to the dialysate fluid in the dialysate circuit by closing the BRV and activating the blood pump, such that:

at least a portion of the blood plasma component of the blood contained in the blood side of the dialyser is forced across the blood filter to the dialysate side and mixes with dialysate solution contained therein,
the mixing of the at least a portion of the blood plasma component with the clean dialysate solution results in the production of spent dialysate solution, and
the spent dialysate solution is forced from the dialysate side into the first pump chamber.

The method may also include deactivating the blood pump and opening the blood return valve, configuring of one or more of the plurality of valves in a fourth configuration, pumping the spent dialysate solution from the first pump chamber into the dialysate side of the dialyser, whereby the portion of the blood plasma component contained in the spent dialysate solution passes back across the blood filter to the blood side of the dialyser, and pumping blood from the blood side of the dialyser back to the patient via the blood return line and venous access line.

These and other embodiments, as well as other objects and advantage thereof, will become even more apparent with reference to the following detailed description and accompanying drawings.

DETAILED DESCRIPTION OF SOME OF THE EMBODIMENTS

Figure 1:
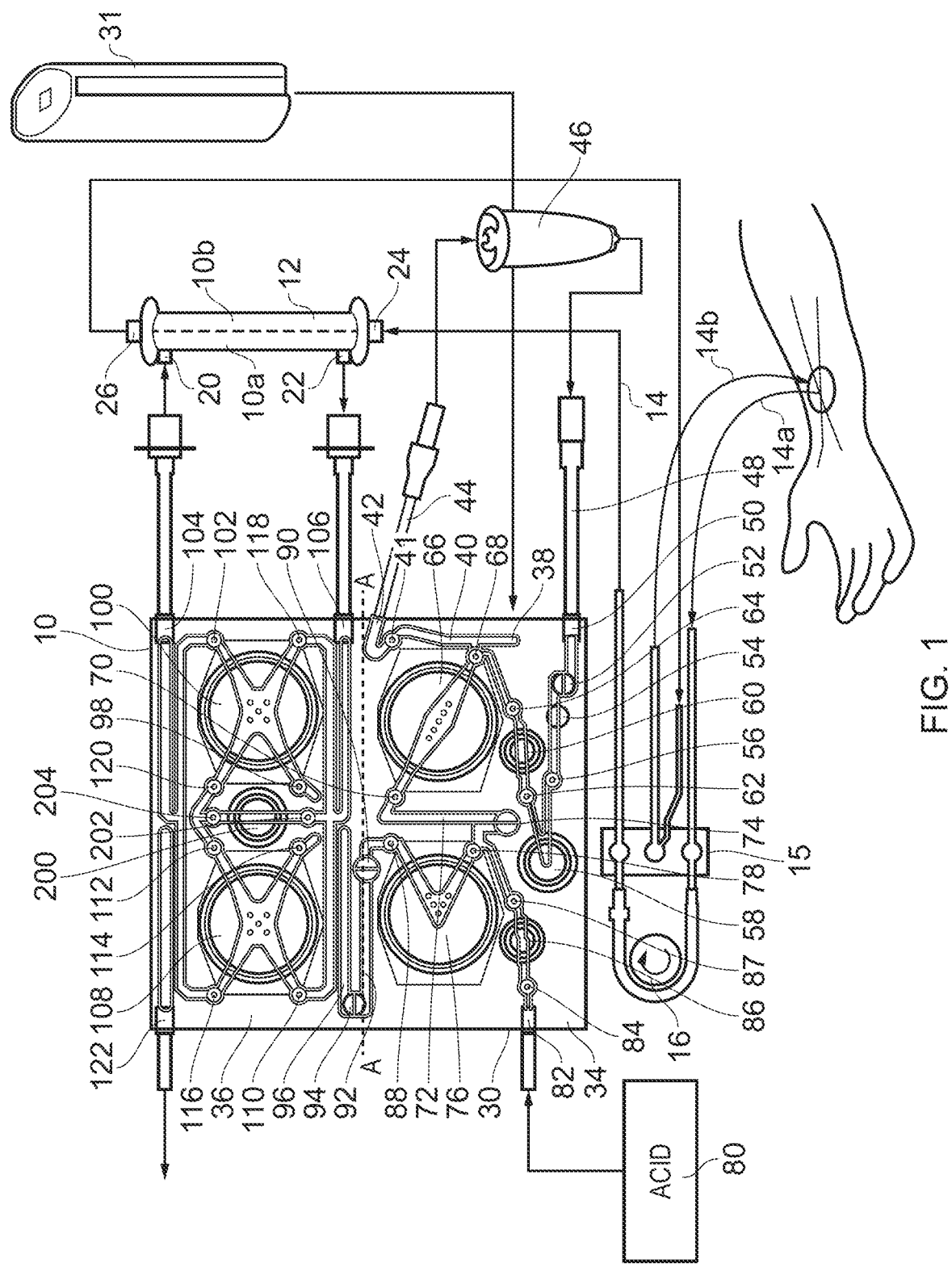
FIG. 1 shows a schematic of a dialysis system having a disposable cartridge comprising a fluid path defined by pumps and valves.
Figure 1A:
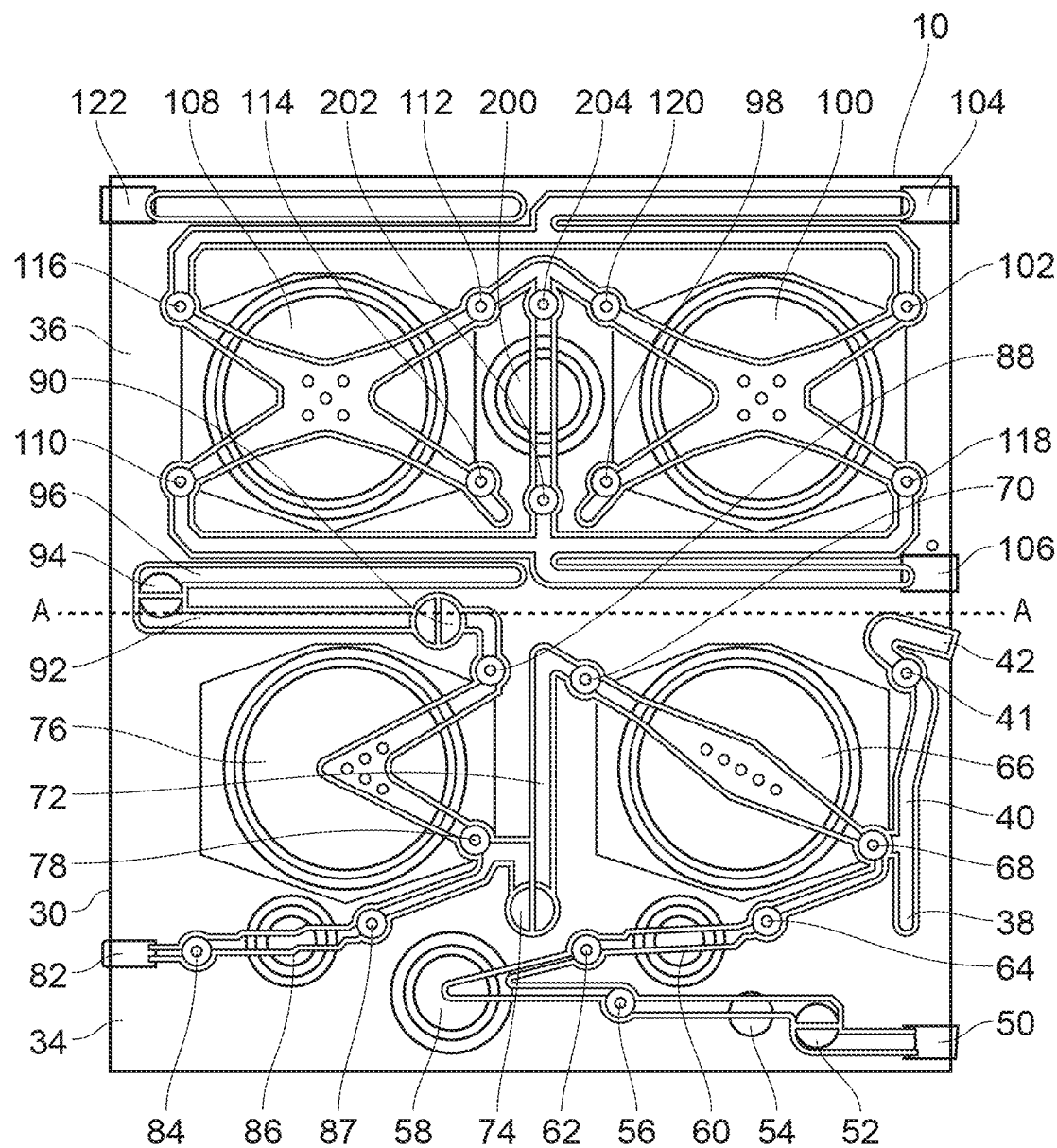
FIG. 1a shows a detailed schematic view of the cartridge of FIG. 1.

Referring to FIGS. 1 and 1a, a dialysis system, generally referred to as 10, is shown. A dialyser 12 receives blood via a blood removal venous line 14a connected to a patient by a vascular access device (not shown for clarity), for example a hollow needle as typically used for drawing blood from a patient. The blood is pumped from the patient via a blood pressure sensor module 15 to the dialyser by a peristaltic pump 16. The blood passes through the dialyser 12 in a known manner and is returned to the patient via a return venous line 14b connected to the same vascular access device as the blood removal venous line 14a. The dialyser 12 comprises a cylindrical tube closed by opposing ends. A semi-permeable membrane (not shown) is provided within the dialyser tube and separates the patient's blood from a dialysate (cleaning) solution. The membrane extends substantially between the opposing ends of the cylinder. The dialysate solution removes impurities from the patient's blood in a known manner.

The dialyser has an inlet 20 for receiving clean dialysate solution and an outlet 22 for removing spent dialysate solution from the dialyser 12. The dialyser also has an inlet 24 for receiving untreated blood from the peristaltic pump 16 and an outlet 26 for returning processed blood to the patient. The dialyser 12 is typically provided in a substantially upright orientation, in use, with the patient's blood flowing longitudinally through the dialyser 12 from the blood inlet 24 to the blood outlet 26. The dialysate solution inlet 20 and dialysate solution outlet 22 are configured to be orientated substantially orthogonal to the blood inlet 24 and blood outlet 26, and to provide a counter-flow. Dialysate solution is circulated through the haemodialysis machine at a fluid flow rate in the region of 400 ml/min for approximately four hours.

The semi-permeable membrane in the dialyser divides the system 10 into a dialysate side 10a and a blood side 10b.

The dialysis system 10 defines a fluid circuit including a cartridge 30, as will now be described. The cartridge 30 is a consumable component in the haemodialysis machine described.

The cartridge 30 is formed from an acrylic plastic such as SG-10 and has a machine side and a patient side. The cartridge 30 defines pump chambers which are closed by respective diaphragms, formed from, for example, DEHP-free PVC, to define respective pumps. In this embodiment, each diaphragm is part of a single, common sheet of material applied to the cartridge 30. The individual diaphragms are operable by pneumatic pressure applied thereto.

A series of flow paths are formed in the cartridge 30 for carrying dialysate solution constituted from water, bicarbonate solution and acid solution. The flow paths are located between the sheet of material closing the machine side of the cartridge 30 and a further sheet of the same material closing the patient side of the cartridge 30.

The cartridge 30 is inserted into a machine which is provided with a series of pneumatic pumps and valves and a corresponding, opposing layout of pump chambers to match the cartridge pump chambers.

In use, a pressure source applies either a positive or negative pressure to one side of the diaphragm of each pump chamber, as required, pulling and pushing the diaphragm back and forth to pump fluid through the fluid paths in the cartridge 30, in a circuit defined by a plurality of valves, which also work by movement of the membrane back and forth The valves of the cartridge 30 are conventional diaphragm valves defined by respective openings in the cartridge 30 and closed by respective flexible diaphragms. Each valve is operable by applying a negative pressure to the diaphragm to open the valve and applying a positive pressure to the diaphragm to close the valve. The diaphragm of each valve is part of the single, common sheet of material applied to the machine side of the cartridge 30. The valves are opened and closed according to a flow control strategy, as will become apparent.

The machine side of the cartridge 30 abuts a pump driver (not shown) comprising a platen having a plurality of recessed surfaces, each recessed surface substantially corresponding in geometry and volume to a pump chamber defined in the cartridge 30. Each recessed surface has a fluid port connectable with a source of positive fluid, pressure and, with a source of negative fluid pressure via a valve.

The positive and negative fluid pressure sources, typically pneumatic pressure, include a pressure pump and a vacuum pump respectively. When the valve is operated to allow fluid to flow into a recessed surface from the source of positive fluid pressure, the diaphragm moves into a corresponding pump chamber and any fluid, i.e. dialysate solution, therein is expelled from that pump chamber via the series of flow paths. When the valve is operated to allow fluid to flow out of a recessed surface to the source of negative fluid pressure, the diaphragm is moved away from a pump chamber and into the corresponding recessed surface to permit fluid to be drawn into that pump chamber via the series of flow paths. The surface of the pump chambers and of the platen provide a positive stop for each diaphragm, to prevent overstretching thereof. The positive stop ensures that the volume of fluid drawn into and pumped from the pump chambers is accurately controlled.

Figure 2:
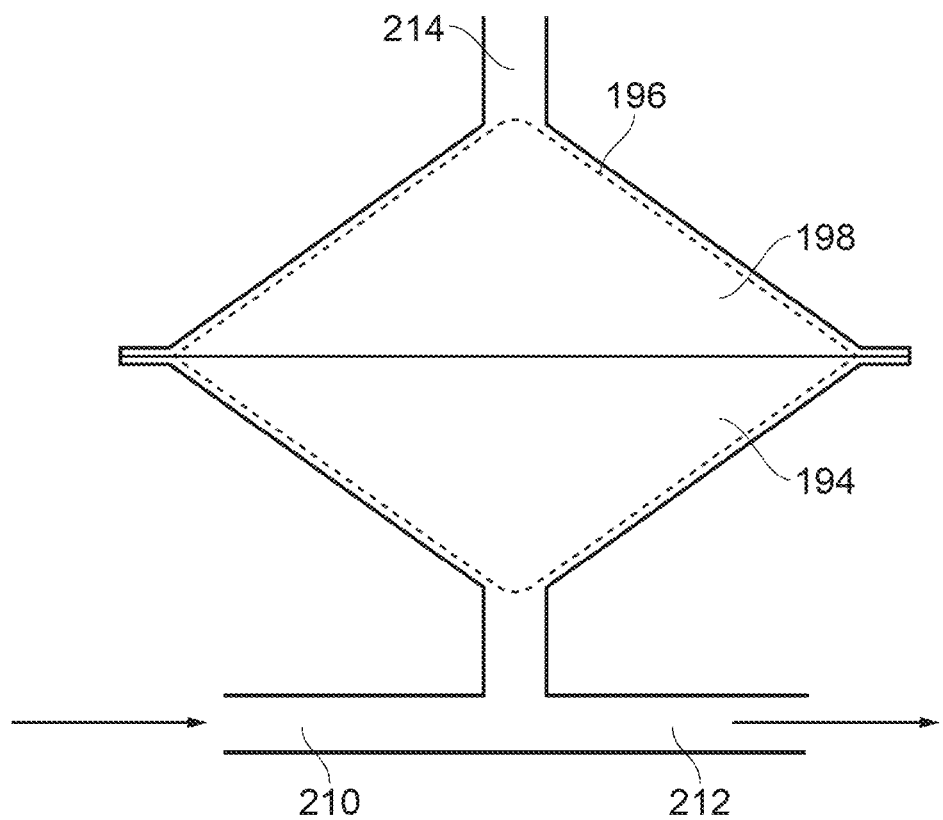
FIG. 2 shows a schematic view of the operation of a pump of the type defined by the disposable cartridge.

The cartridge 30 has two main functions, preparation of dialysate solution and flow balance. Each function is performed by a separate part of the cartridge as illustrated in FIGS. 1 and 2 by the schematic separation of the cartridge into two parts by the line A-A in the figures. The dialysate preparation function is performed by one part of the cartridge, generally referred to at 34 and the flow balance function is performed by the other part of the cartridge, generally referred to at 36. The cartridge 30 prepares an accurately mixed homogenous dialysate solution and ensures that the flow of clean dialysate supplied to the dialyser 12 matches (to within clinical tolerances) the volume of spent dialysate drawn from the dialyser 12.

The cartridge 30 is provided with a plurality of connections to and from the cartridge 30 as described below.

A first inlet port 38, from hereon referred to as the water inlet port, defined in the machine side of the cartridge 30 receives purified water from a purified water supply 31 such as a reverse osmosis water supply.

A first outlet port 42, from hereon referred to as the water outlet port, defined in an edge of the cartridge 30 directs the purified water to a first dialysate solution constituent which, in the illustrated embodiment shown in FIGS. 1 and 1a, is bicarbonate 46.

A second inlet port 50, from hereon referred to as the bicarbonate inlet port, defined in the same edge of the cartridge 30 as the water outlet port 42 receives purified water mixed with the bicarbonate 46.

A third inlet port 82, from hereon referred to as the acid inlet port, defined in the opposite edge of the cartridge 30 to the water outlet port 42 and bicarbonate inlet port 50 receives a second dialysate solution constituent which, in the illustrated embodiment shown in FIGS. 1 and 1a, is acid 80.

A second outlet port 104, from hereon referred to as the clean dialysate solution outlet port, is defined in the same edge of the cartridge as the water outlet port 42 and the bicarbonate inlet port 50. The clean dialysate outlet port 104 directs clean dialysate solution to the dialyser 12.

A fourth inlet port 106, from hereon referred to as the spent dialysate solution inlet port, is defined in the same edge of the cartridge 30 as the water outlet port 42, bicarbonate inlet port 50 and clean dialysate outlet port 104. The spent dialysate solution inlet port 106 receives spent dialysate solution from the dialyser 12.

A third outlet port 122, from hereon referred to as the drain port, is defined in the same edge of the cartridge as the acid inlet port 82. The drain port 122 directs spent dialysate solution out of the cartridge 30.

Dialysate Preparation According to Some Embodiments

Dialysate solution is prepared in the cartridge 30 by combining purified water with two dialysate constituents, namely a bicarbonate solution and an acid solution.

Purified water is admitted into the cartridge 30 from a purified water supply 31 via the water inlet port 38. The purified water passes through a channel 40 via a water inlet valve 41, when open, and exits the cartridge 30 at the water outlet port 42. From here, the purified water is carried by a tube 44 through a bicarbonate cartridge 46 in a known manner to generate a purified water and bicarbonate solution. The purified water and bicarbonate solution is carried by a tube 48 and re-admitted into the cartridge 30 via the bicarbonate inlet port 50.

The temperature of the bicarbonate solution is measured at sensing port 52 and the bicarbonate solution pressure is measured at sensing port 54. The bicarbonate solution passes a bicarbonate control valve 56, when open, before entering a bicarbonate solution reservoir 58 having an inlet and an outlet. The bicarbonate control valve 56 is closed when flow therethrough is not required.

A bicarbonate dosing pump chamber 60 has an inlet and an outlet and receives the bicarbonate solution from the bicarbonate solution reservoir 58 through a bicarbonate dosing pump inlet valve 62. The bicarbonate dosing pump chamber 60 is closed by a diaphragm to define a bicarbonate dosing pump which, upon actuation of the diaphragm, pumps the bicarbonate solution from the bicarbonate dosing pump 60 to a first mixing pump chamber 66 (bicarbonate pump chamber). The bicarbonate dosing pump 60 has a bicarbonate dosing pump outlet valve 64 which is closed when the bicarbonate dosing pump inlet valve 62 is open. The bicarbonate dosing pump outlet valve 64 is opened to permit bicarbonate solution to be pumped to the bicarbonate pump chamber 66. When the bicarbonate dosing pump outlet valve 64 is open, the bicarbonate dosing pump inlet valve 62 is closed to prevent bicarbonate solution from being pumped back into the bicarbonate solution reservoir 58.

The bicarbonate pump chamber 66 having an inlet and an outlet receives the purified water and bicarbonate solution from the bicarbonate dosing pump 60 via a bicarbonate pump inlet valve 68. The bicarbonate pump inlet valve 68, when open, can also admit purified water into the bicarbonate pump chamber 66 from the water inlet port 38. The bicarbonate pump chamber 66 is closed by a diaphragm to define a pump which, upon actuation of the diaphragm, pumps the bicarbonate solution and purified water therein through a bicarbonate pump outlet valve 70 to a second mixing pump chamber 76 (acid pump).

When the bicarbonate pump inlet valve 68 is open, the bicarbonate pump outlet valve 70 and water outlet valve 41 are closed. When the bicarbonate pump outlet valve 70 is open, the bicarbonate pump inlet valve 68 is closed to prevent the bicarbonate and purified water solution from being pumped back into channel 40.

From the bicarbonate pump outlet valve 70, the bicarbonate and purified water solution enters a sensor channel 72 in which the haemodialysis machine measures the conductivity of the bicarbonate and purified water solution in a known manner. The bicarbonate and purified water solution then enters a temperature sensor 74 before, if the conductivity and temperature of the bicarbonate and purified water solution are within tolerance, entering the acid pump chamber 76.

The acid pump chamber 76 having an inlet and an outlet receives the bicarbonate and purified water solution from the bicarbonate pump 66 via an acid pump inlet valve 78. The acid pump inlet valve 78, when open, can also admit an acid solution into the pump chamber 76. The acid pump chamber 76 is closed by a diaphragm to define a pump which, upon actuation of the diaphragm, pumps the acid solution, bicarbonate solution and purified water therein through an acid pump outlet valve 88 to the first flow balance pump chamber 100. When the acid pump inlet valve 78 is open, the acid pump outlet valve 88 is closed. When the acid pump outlet valve 88 is open, the acid pump inlet valve 78 is closed.

The acid solution is admitted into the cartridge 30 from a pre-determined supply of acid 80 via the acid solution inlet port 82. From the acid solution inlet port the acid solution passes through an acid dosing pump chamber 86 via an acid dosing pump inlet valve 84 and an acid dosing pump outlet valve 87. The acid dosing pump outlet valve 87 is closed when the acid dosing pump inlet valve 84 is open. The acid dosing pump inlet valve 84 is closed when the acid dosing pump outlet valve 87 is open.

The dialysate solution exits the acid pump chamber via the acid pump outlet valve 88 and passes through a first dialysate solution temperature sensor 90 and a first dialysate solution conductivity sensor 92. A second dialysate solution temperature sensor 94 and a second dialysate solution conductivity sensor 96 are provided to corroborate the data provided by the first dialysate solution temperature sensor 90 and the first dialysate solution conductivity sensor 92. Providing the data measured by sensors 90, 92, 94 and 96 is within tolerance, the dialysate solution is admitted into a first flow balance pump chamber 100

Flow Balance According to Some Embodiments

The flow balance function of the cartridge 30 provides first and second flow balance pump chambers 100, 108, each having two inlets and two outlets to define two independent flow paths therethrough. The first and second flow balance pump chambers 100, 108 are of substantially equal volume. Either the first or second flow balance pump chamber 100, 108 pumps dialysate solution to a dialyser 12 and the other of the first or second flow balance pump chambers 100, 108 pumps dialysate solution from the dialyser 12 to the drain port 122. After every approximately 20 strokes of the first and second flow balance pumps 100, 108, their function is reversed.

From this point onwards, dialysate solution will be referred to as either clean dialysate solution or spent dialysate solution. Clean dialysate solution is intended to mean dialysate solution that is either new dialysate solution or clean dialysate solution that has been treated to remove waste product therefrom. Spent dialysate solution is intended to mean dialysate solution that has passed through the dialyser 12 to remove waste fluids from a patient's blood into the dialysate solution.

Each of the first and second flow balance pump chambers 100, 108 are closed by a diaphragm to define respective pumps. The diaphragm is actuated away from a pump chamber by a negative pressure source to draw a volumetrically measured quantity of dialysate solution into the pump chamber. The diaphragm is actuated toward the pump chamber to pump the fluid therein out of an outlet.

The first flow balance pump chamber 100 has a clean dialysate solution inlet valve 98 for receiving clean dialysate solution from the acid pump 76 and a clean dialysate solution outlet valve 102 for pumping clean dialysate solution to the dialyser 12. The first flow balance pump chamber 100 also has a spent dialysate solution inlet valve 118 for receiving spent dialysate from the dialyser 12 and a spent dialysate solution outlet valve 120 for pumping the spent dialysate to drain via drain outlet port 122.

At any one time, only one of valves 98, 102, 118 or 120 will be open and the other three valves will be closed. The flow balance function, as described above, requires alternating the function of each flow balance pump approximately every 20 cycles. Therefore, when the first flow balance pump 100 is pumping clean dialysate solution to the dialyser 12, only valves 98 and 102 are in use and when the first flow balance pump 100 is pumping spent dialysate solution from the dialyser 12 to drain, only valves 118 and 120 will be in use.

The clean dialysate solution is pumped out of the first flow balance pump chamber 100 through the first flow balance pump clean dialysate solution outlet valve 102, upon closure of the first flow balance pump clean dialysate inlet valve 98, to the dialyser 12 via the dialyser outlet port 104.

Spent dialysate solution returns to the cartridge 30 from the dialyser 12 via the dialyser inlet port 106. The second flow balance pump chamber 108 has a spent dialysate solution inlet valve 110 for receiving spent dialysate solution from the dialyser 12 and a spent dialysate solution outlet valve 112 for pumping the spent dialysate solution to drain via drain outlet port 122. The second flow balance pump 108 also has a clean dialysate solution inlet valve 114 for receiving clean dialysate solution from the acid pump chamber 76 and a clean dialysate solution outlet valve 116 for pumping clean dialysate solution to the dialyser 12.

At any one time, only one of valves 110, 112, 114, 116 will be open and the other three valves will be closed. When the second flow balance pump 108 is pumping clean dialysate solution to the dialyser 12, only valves 114 and 116 will be in use and when the second flow balance pump 108 is pumping spent dialysate solution from the dialyser 12 to drain, only valves 114 and 116 will be in use.

In the illustrated example, the operation of the first and second flow balance pumps 100, 108 can be switched so that the first flow balance pump 100 is used to draw spent dialysate solution from the dialyser 12 and the second flow balance pump 108 is used to pump clean dialysate solution into the dialyser 12 as described below.

The clean dialysate solution is drawn into the second flow balance pump chamber 108 from the acid pump 76 via the second flow balance pump clean dialysate solution inlet valve 114 upon actuation of the diaphragm. The clean dialysate solution is then pumped from the second flow balance pump chamber 108 via the second flow balance pump clean dialysate solution outlet valve 116, upon closure of the clean dialysate solution inlet valve 114, to the dialyser 12.

Spent dialysate solution from the dialyser 12 is drawn into the first flow balance pump 100 via the second flow balance pump spent dialysate solution inlet valve 118. The spent dialysate solution is then pumped out of the first flow balance pump chamber 100 via the second flow balance pump spent dialysate solution outlet valve 120, upon closure of the spent dialysate solution inlet valve 118, to drain via drain outlet port 122.

The volume of fluid that is returned from the dialyser 12 is greater than the volume of fluid that is pumped to the dialyser via the first or second flow balance pump 100, 108. The first and second flow balance pumps have fixed volumes meaning that the excess fluid volume cannot be accommodated in the first or second flow balance pump.

An ultrafiltration pump 200 is provided between the first and second flow balance pumps 100, 108 and has an inlet valve 210 and an outlet valve 212. The ultrafiltration pump 200 comprises a concave recess in the cartridge closed by a flexible diaphragm, the concave recess and the flexible diaphragm defining an ultrafiltration pump chamber.

In use, the inlet valve 210 of the ultrafiltration pump 200 is opened to allow the ultrafiltration pump to draw in a pre-determined volume of spent dialysate solution. When the inlet valve 210 of the ultrafiltration pump is open, the outlet valve 212 of the ultrafiltration pump 200 is closed. When the ultrafiltration pump 200 has received a volume of spent dialysate solution, the outlet valve 212 is opened and the spent dialysate solution in the ultrafiltration pump chamber is pumped through the outlet valve 212 to drain via the drain outlet port 122. When the outlet valve 212 of the ultrafiltration pump 200 is open, the inlet valve 210 of the ultrafiltration pump 200 is closed.

The purpose of the ultrafiltration pump is to remove excess fluid generated by the patient. By separating the ultrafiltration pump operation from the flow balance pumps and by employing a pump arrangement described herein, fluid can be removed from the dialyser at appropriate intervals between the stages of the operation of the flow balance pumps, without requiring modification to the flow balance pump operation. Usually, the ultrafiltration pump will remove fluid from the dialyser during a pump swapping operation of the flow balance pumps and this may be done in the range of once every 10 to once every 30 flow balance pump cycles. Typically, fluid is removed from the dialyser by the ultrafiltration pump approximately up to once every pump cycle.

FIG. 2 shows a representative view of a flow balance pump 100 according to the present disclosure. The flow balance pump chamber 194 is provided on the cartridge and is closed by a diaphragm 196 which, at rest, sits across the pump chamber 194. The pump chamber receives either clean or spent dialysate solution via a dialysate solution inlet port 210 and pumps dialysate solution from the pump chamber via a dialysate solution outlet port 212.

The cartridge 30 is removably mounted into a haemodialysis machine which has a flow balance pump cavity 198 substantially corresponding in dimension and shape to the pump chamber 194. Upon supply of positive or negative pressure via a pump cavity pressure inlet port 214, the diaphragm is actuated into either the pump chamber 194 or pump cavity 198 to either draw fluid into the pump chamber 194 or pump fluid from the pump chamber 194.

Operation of the Device According to Some Embodiments

Figure 3:
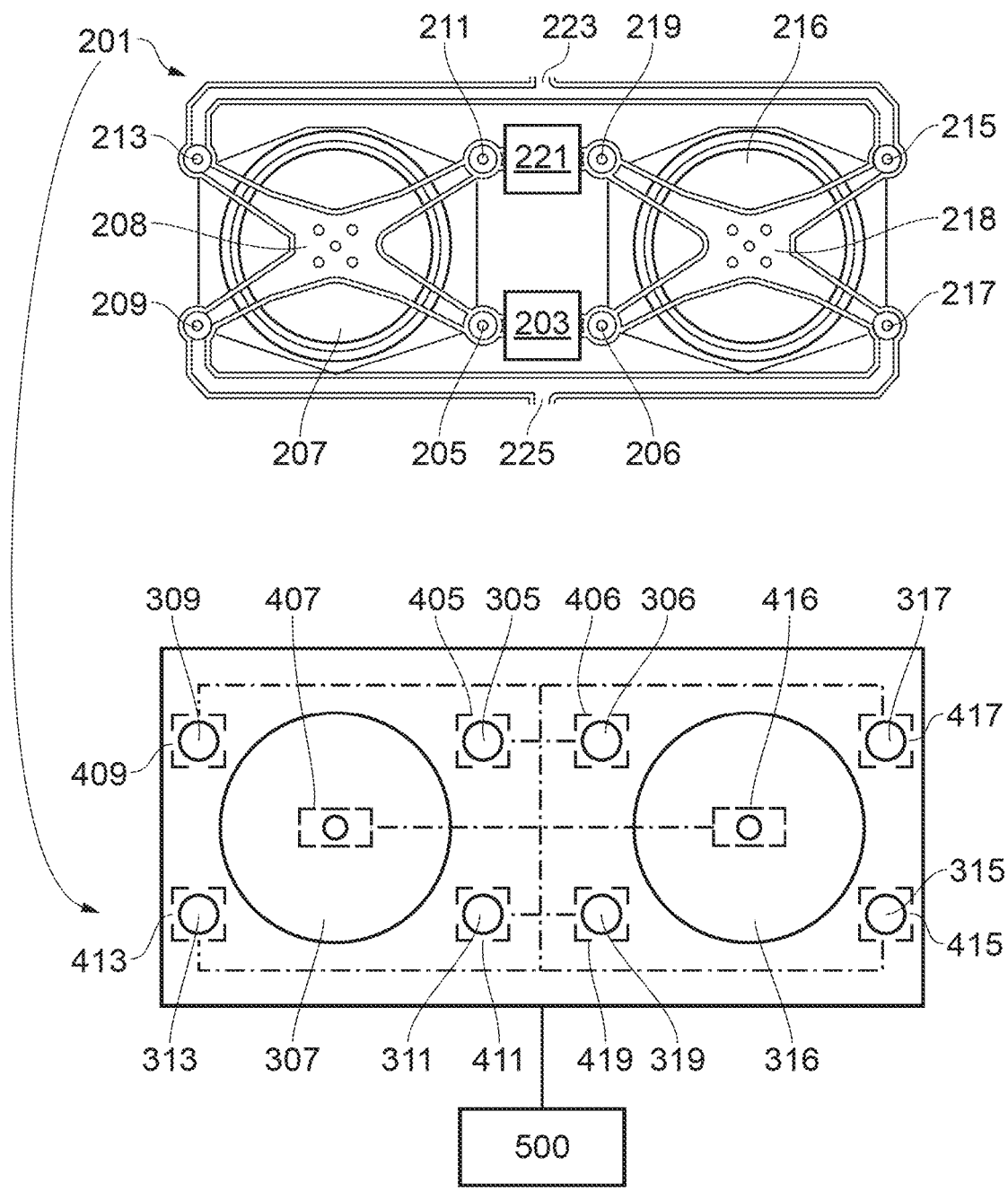
FIG. 3 shows a schematic view of the pump and valve arrangement of the disclosure.

FIG. 3 shows a schematic representation of the pump and valve arrangement 201 of the disclosure. In this case, the pump and valve arrangement 201 is provided by the combination of a membrane pump cartridge (or part cartridge) and a vacuum pump array with platen. The membrane pump cartridge is similar in layout to the flow balance pump arrangement described above.

The membrane pump cartridge comprises first and second source valves 205, 206, first and second pumps 207, 216 and first and second pump chambers 208, 218, first and second dialyser inlet valves 209, 217 and first and second dialyser outlet valves 213, 215.

The vacuum pump array and platen comprises a platen having a pattern of circular depressions which correspond in position and size to the valves and pumps on the pump cartridge. In the figure, these are numbered 100 higher than the membrane pump features.

Each depression has an aperture at the base thereof which is in fluid communication with an associated vacuum pump. Each vacuum pump, shown in broken lines as they sit on the rear face of the platen, is numbered 100 higher than the respective associated platen feature.

All of the vacuum pumps are connected to a control system 500. The control system 500 is a microprocessor which operates the vacuum pumps 405-419 in a manner so as to effect either haemodiafiltration or haemodialysis. The connection to the pumps may be wired or wireless. Wireless connection options include IR, Bluetooth or WIFI, amongst others.

The dialysate is produced elsewhere on the cartridge by mixing acid and bicarbonate compounds with a set volume of de-ionised, water provided by a reverse osmosis machine which has been sterilised as is described above. This forms the source of dialysate 327 used by the pump and valve arrangement 201.

By selectively operating the vacuum pumps, the control system controls the opening and closure of the valves as well as actuation of the first and second pumps. The microprocessor control system is programmable to operate the valves in a variety of different configurations. Based on the programming of the controller, the controller will communicate with each of the valves or means for operating the valves, so that each valve may be opened and closed independently based on the programming entered into the controller by the user, skilled operator or programme instructions.

Although the control system 500 has been described in the specific embodiment as a microprocessor, the control system 500 may instead comprise an electrical switching arrangement or a mechanical control arrangement. In the case of a mechanical control arrangement, rather than individual vacuum pumps for each platen cavity, it is envisaged that a single vacuum pump would apply a negative pressure to the platen and a mechanical camming or gearing arrangement would actuate valves on the platen to control the application of the negative/positive pressure selectively according to the required operating mode.

Referring to FIGS. 4a to 4e, a dialysis system 10 in accordance with the first aspect of the disclosure operating a method in accordance with the second aspect of the disclosure is shown schematically. FIGS. 4a to 4e show a simplified view of the system shown in FIG. 1 with the water supply, bicarbonate cartridge and acid supply omitted for clarity. Also, the representation of the mixing part of the cartridge 34 of the cartridge 30 has been simplified but corresponds to the arrangement shown in FIGS. 1 and 2. The system 10 comprises a blood circuit and a dialysate circuit. The blood circuit comprises the blood removal line 14a, the blood pressure sensor modular 15, a tube set 17 of the peristaltic pump 16, the dialyser 12, a blood accumulator chamber and the blood return line 14b, which has a blood return line closure thereon in the form of a venous clamp 124. The dialysate fluid circuit comprises the first and second flow balance pumps, the clean dialysate solution inlet line and the spent dialysate solution outlet line and the drain outlet line.

Figure 4A:
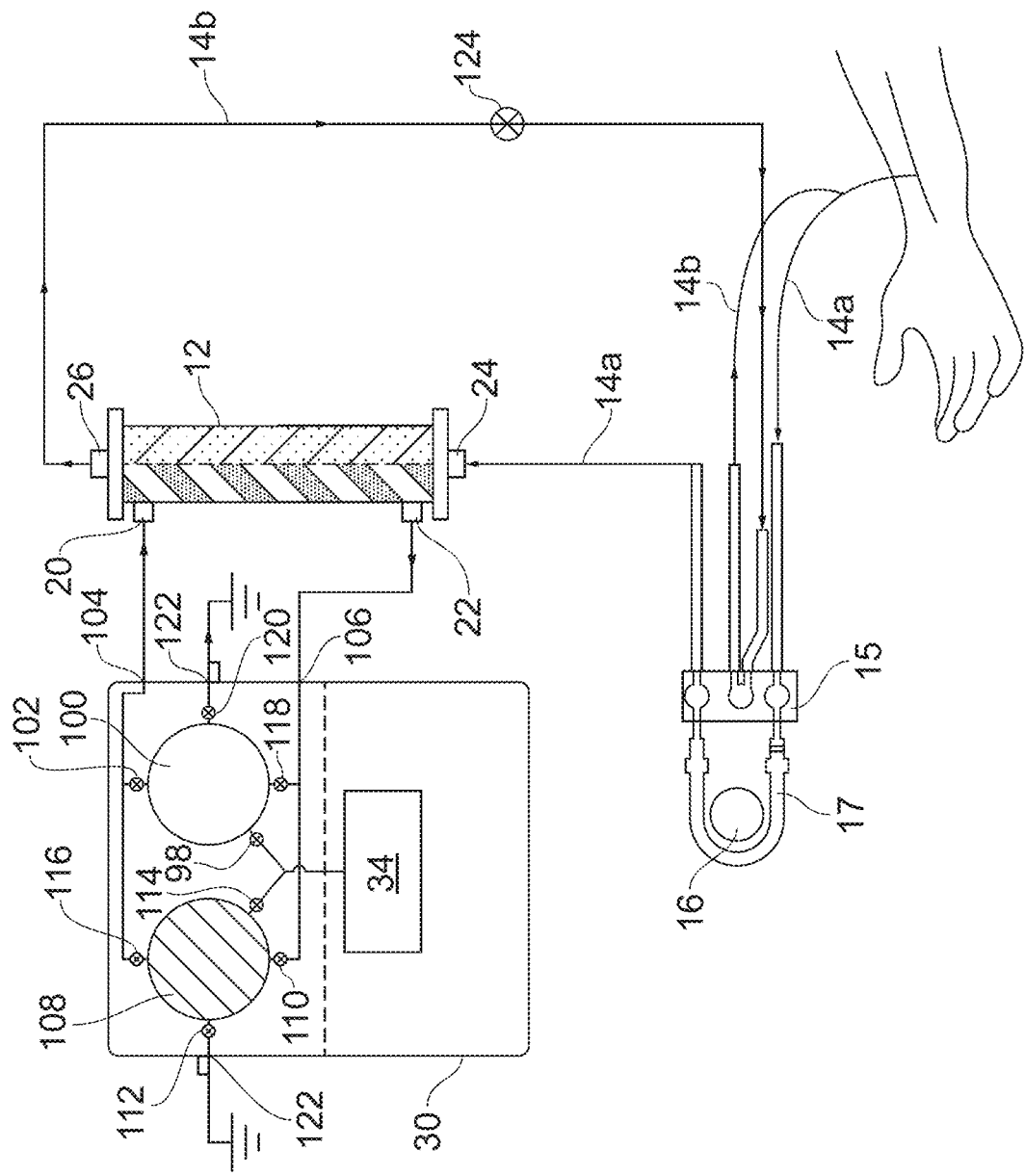
FIGS. 4a to 4e are schematic views of a dialysis system in accordance with the first aspect of the disclosure, performing the method of the second aspect of the disclosure.

FIG. 4a illustrates the system in an initial condition. In this condition, the peristaltic pump 16 is inactive and the venous clamp 124 is closed. The first flow balance pump chamber 100 is empty and the second flow balance pump chamber 108 is filled with fresh dialysate solution (represented by the unshaded hatched fluid) previously prepared on the mixture part 34 of the cartridge 30. The dialyser 12 is filled on the blood side of the semi-permeable membrane with blood (represented by the fully shaded oppositely hatched fluid) and on the dialysate side of the semi-permeable membrane with dialysate solution which has drawn waste material out of the blood across the semi-permeable membrane (represented by the alternately shaded hatched fluid). At this point, the control system 500 operates the vacuum pumps 405 to 419 so as to close the valves 98, 102 and 120 of the first flow balance pump 100 and open valve 118 of the first flow balance pump and to close the valves 110, 112, 114 of the second flow balance pump 108 and to open valve 116 of the second flow balance pump 108. The controller then causes the empty flow balance pump 100 to be actuated to draw the spent dialysate from the dialyser 12 via the port 22 and valve 118 into the first flow balance pump chamber. The controller simultaneously causes the second flow balance pump to be actuated to push the clean dialysate solution from the second flow balance pump chamber via the valve 116 and port 104 and 20 into the dialyser.

Figure 4B:
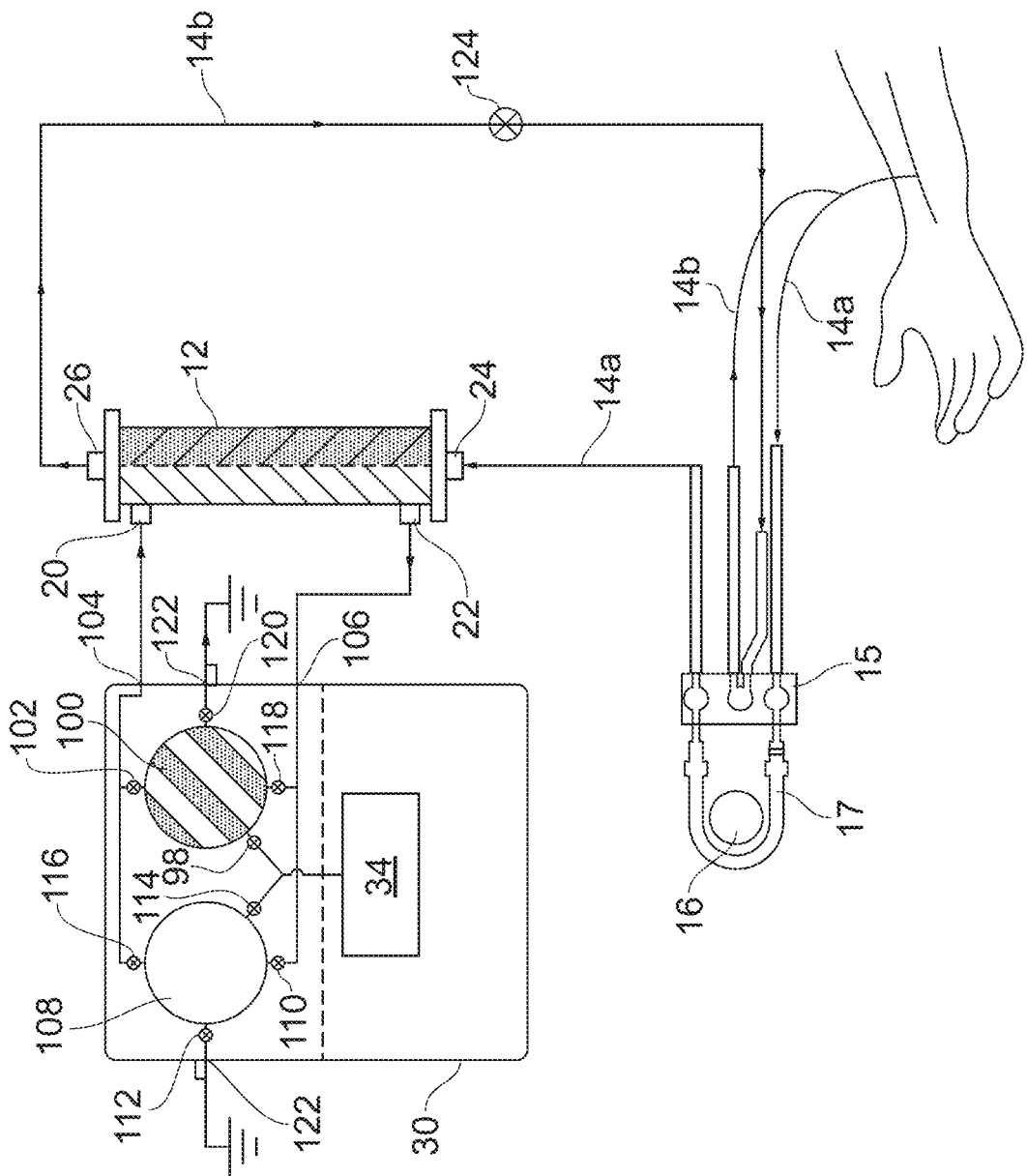

At this point in the method, as shown in FIG. 4b, the first flow balance pump chamber 100 is filled with spent dialysate (as represented by the alternate shaded hatched fluid). The dialysate side of the semi-permeable membrane of the dialyser is filled with clean dialysate fluid (as represented by the unshaded hatched fluid) and the blood side of the dialyser is filled with blood (as represented by the fully shaded and oppositely hatched fluid).

The controller then operates the pneumatic pumps so as to close the valves 98, 102, 118 of the first flow balance pump 100 and the valves 110, 112 and 116 of the second flow balance pump 108 so that the spent dialysate outlet valve 120 of the first flow balance pump 100 and the clean dialysate inlet valve 114 of the second flow balance pump 108 are open. The controller actuates the flow balance pumps 100, 108 again so that the first flow balance pump expels the spent dialysate via the spent dialysate outlet valve 120 to the drain 122 and the second flow balance pump draws clean dialysate from the mixing part 34 of the cartridge 30 via the clean dialysate inlet valve 114 to fill the second flow balance pump 108 with clean dialysate fluid.

Figure 4C:
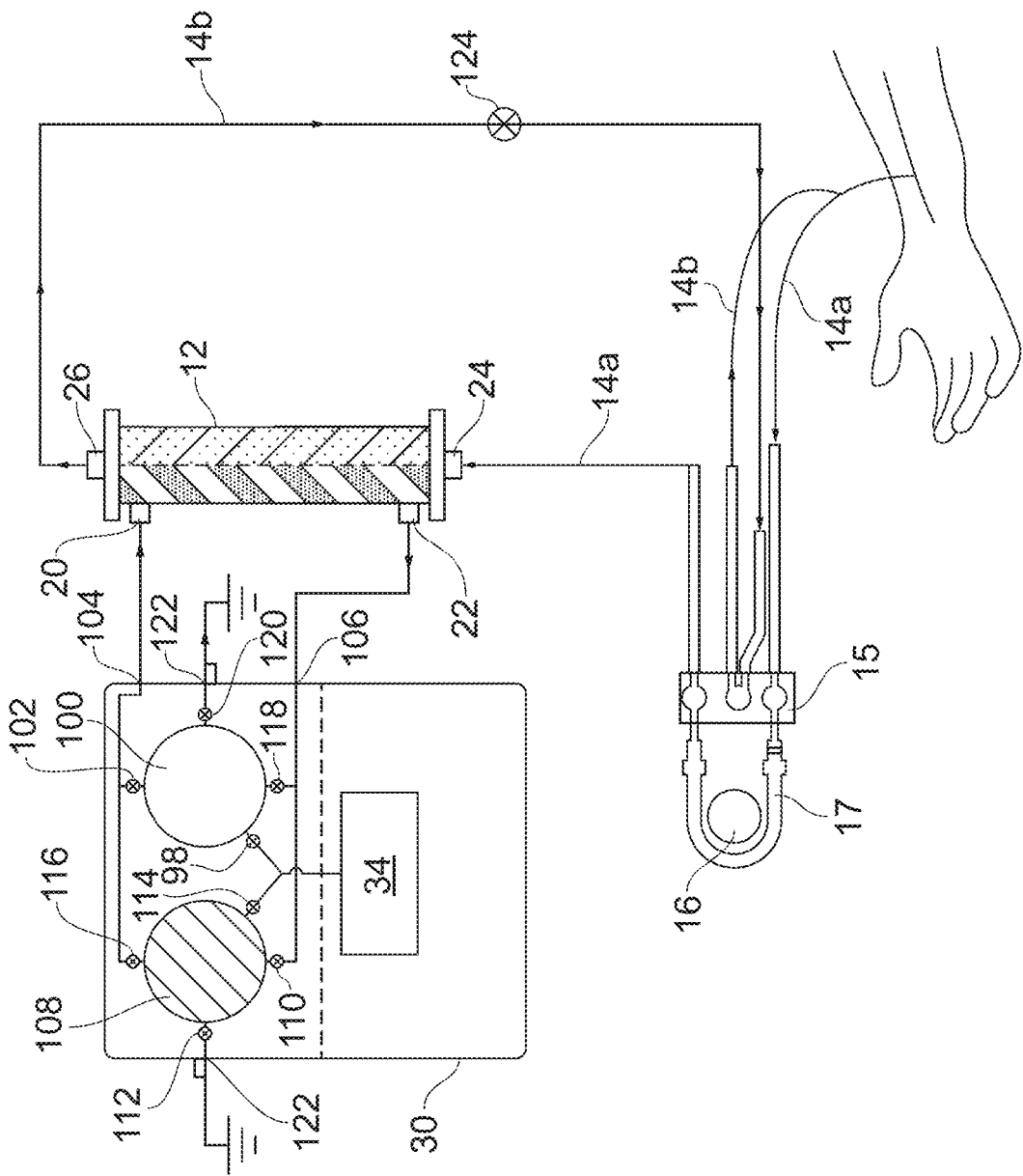

After that step, as represented in FIG. 4c, the first flow balance pump chamber 100 is empty, the second flow balance pump chamber 108 is filled with clean dialysate solution (as illustrated by the unshaded hatched fluid), the dialysate side of the semi-permeable membrane of the dialyser 12 is filled with spent dialysate fluid (as illustrated by the alternately shaded hatched fluid) and the blood side of the semi-permeable membrane in the dialyser is filled with blood.

Figure 4D:
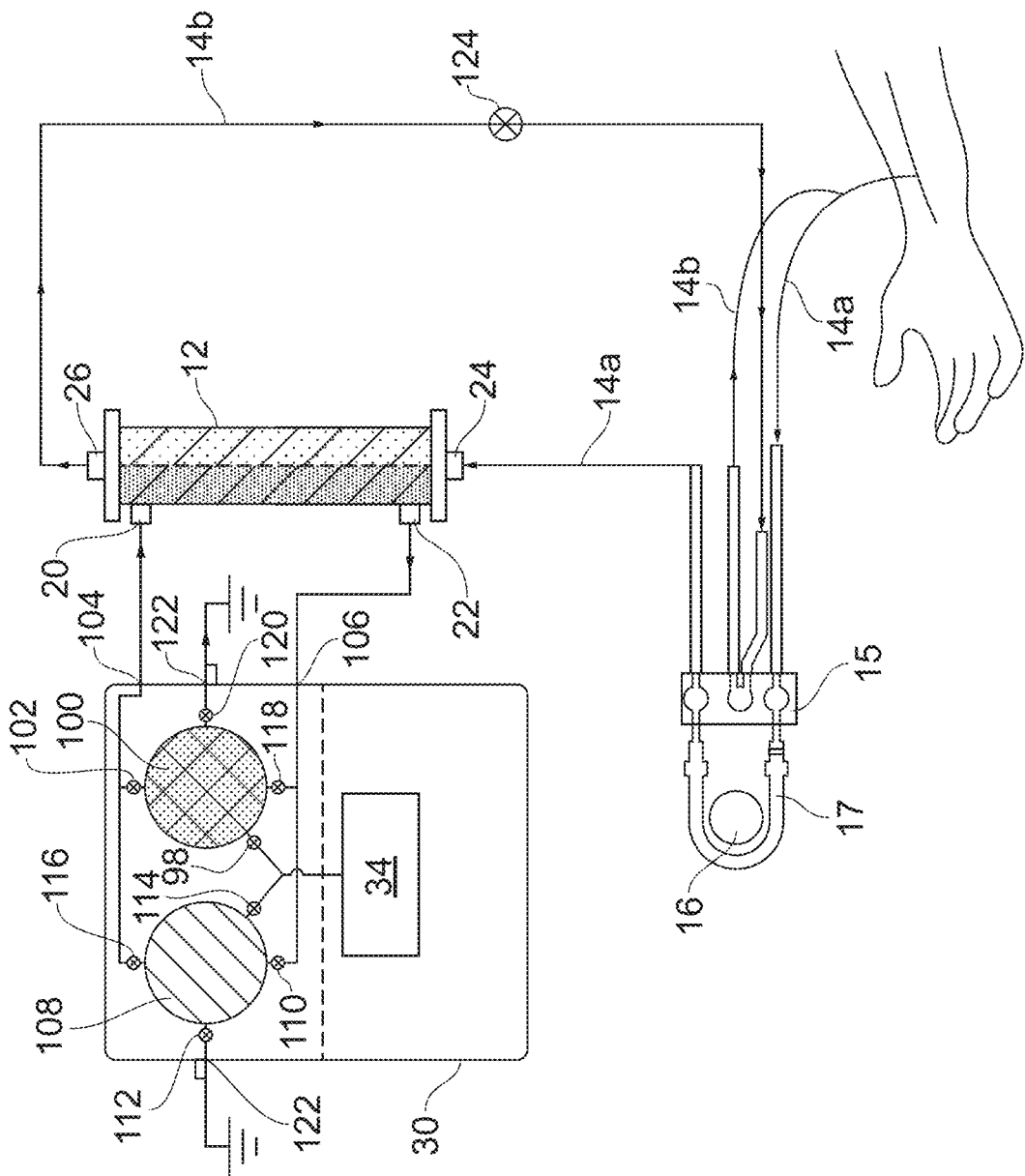
Figure 4E:
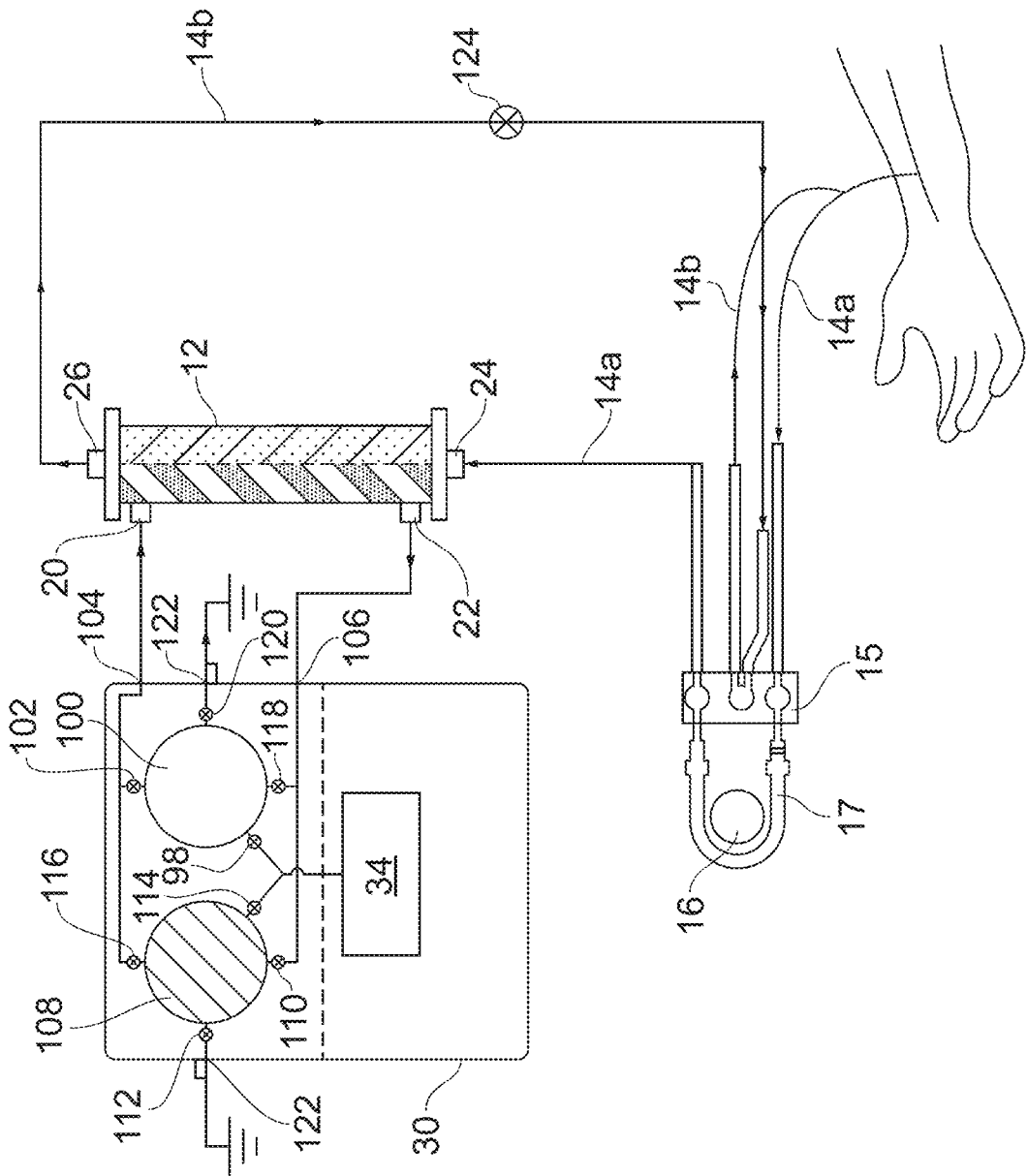

At this point, the controller closes the valves 98, 102 and 120 of the first flow balance pump, leaving valve 118 open and closes all of the valves 110, 112, 114, 116 of the second flow balance pump. The controller activates the peristaltic pump to draw blood from the patient via the venous access and the blood removal line 14a. The controller closes the venous clamp 124 so that the blood in the blood circuit becomes pressurised relative to the dialysate fluid in the dialysate circuit. Because of the pressure differential across the semi-permeable membrane in the dialyser, the blood plasma component of the blood in the dialyser 12 is forced across the semi-permeable membrane to mix with the spent dialysate solution on the dialysate side of the semi-permeable membrane and this, in turn, forces the spent dialysate blood component mixture into the first flow balance pump chamber 100. At this point, a proportion of the blood removed from the patient is on the dialysate side of the semi-permeable membrane in the first flow balance pump chamber. As such, the first flow balance pump chamber 100 is acting as a blood accumulator. This mixed dialysate solution/blood plasma is shown in FIG. 4d as a fully shaded and cross-hatched fluid in the first flow balance pump chamber 100. Moreover, the action of pressurising the blood side of the dialyser forces blood plasma onto the dialysate side of the semi-permeable membrane in the dialyser as represented by the fully shaded hatched fluid in FIG. 4d.

Then, the controller deactivates the peristaltic pump and acts to close the valves 98, 118 and 120 of the first flow balance pump, maintaining all of the valves of the second flow balance pump 108 closed and opening the venous clamp 124. The controller then causes the first flow balance pump 100 to be actuated, pushing the spent dialysate solution/blood plasma mixture back out of the first flow balance pump chamber (blood accumulator) and into the dialyser 12. The blood plasma component of the dialysate solution/blood plasma mixture will pass back across the semi-permeable membrane in the dialyser 12 and return via blood return line 14b to the patient. At the end of that step, the system returns to the condition shown in FIG. 4a.

By means of this process, a single venous access can be used both for removal of blood from the patient and return of blood to the patient and by pushing blood across onto the dialysate side of the semi-permeable membrane, using the flow balance pump chambers as a blood accumulator, blood plasma is pushed across semi-permeable membrane which has a similar effect to haemodiafiltration.

A method of testing the system is disclosed and in such a case, the blood from a patient is replaced by a source of blood analogue fluid. The blood analogue fluid is a fluid which behaves in a similar fashion to blood. The blood analogue fluid preferably includes markers such as a dye to allow an observer to confirm that components of the blood analogue fluid are passed across the semi-permeable membrane into, and mixed together with, the spent dialysate solution then into the first flow balance pump chamber. Furthermore, the blood analogue fluid is preferably Dextran with fluoroscein markers, which can be sensed using an appropriate sensor, such as a fluorometer. This enables the system to be tested to confirm that fluid is passed from the blood side of the semi-permeable membrane to the dialysate side of the semi-permeable membrane and that relevant molecules were removed from the blood analogue fluid when passed back across the semi-permeable membrane from the dialysate side to the blood side of the system.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Some embodiments may be distinguishable from the prior art for specifically lacking one or more features/elements/functionality (i.e., claims directed to such embodiments may include negative limitations).

In addition, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like, are to be understood to be open-ended, i.e., to mean including but not limited to. Only the transitional phrases "consisting of" and "consisting essentially of" shall be closed or semi-closed transitional phrases, respectively (i.e., as set forth in the United States Patent Office Manual of Patent Examining Procedures, Section 2111.03).

What is currently claimed is:

1. A method of operating a dialysis system including
   a blood side,
   a dialysate side containing a dialysate fluid circuit and a blood accumulator chamber, the dialysate fluid circuit comprising a dialysate input pump having a dialysate input pump chamber, and a dialysate output pump having a dialysate output pump chamber,
   a dialyser comprising a fluid chamber, a dialysate inlet, a dialysate outlet, a blood inlet, and a blood outlet,
   a blood circuit comprising a blood pump, the blood accumulator chamber, and a blood return line valve arranged on a blood return line downstream of the dialyser or at the blood outlet of the dialyser, and
   a blood filter arranged within the fluid chamber and dividing the dialysis system into the blood side and the dialysate side, the method comprising:
   closing the blood return line valve; and
   with the blood return line valve closed, operating the dialysate outlet pump or the blood pump to create a pressure differential across the blood filter, the pressure differential forcing blood plasma across the blood filter from the blood side to the dialysate side and into the blood accumulator chamber.

2. A method of operational testing of a dialysis system including a blood side, a dialysate side containing a dialysate fluid circuit and a blood accumulator chamber, the dialysate fluid circuit comprising a dialysate input pump having a dialysate input pump chamber, and a dialysate output pump having a dialysate output pump chamber, a dialyser comprising a fluid chamber, a dialysate inlet, a dialysate outlet, a blood inlet, and a blood outlet, a blood circuit comprising a blood pump, the blood accumulator chamber, and a blood return line valve arranged on a blood return line downstream of the dialyser or at the blood outlet of the dialyser, and a blood filter arranged within the fluid chamber and dividing the dialysis system into the blood side and the dialysate side, the method comprising the following steps:

(a) supplying a dialysate fluid to the dialysate fluid circuit and supplying a blood analogue fluid to the blood circuit;

(b) creating a pressure differential across the blood filter via operation of at least one of the dialysate outlet pump or the blood pump, the pressure differential forcing the blood analogue fluid across the blood filter onto the dialysate side and into the dialysate output pump chamber; and (c) deactivating the blood pump and pushing the blood analogue fluid, via operation of the dialysate outlet pump, back across the blood filter onto the blood side of the dialysis system.

3. The method of claim 2, wherein step (b) includes a first step (b1) comprising deactivating the blood pump, closing the blood return line valve, filling the dialysate input pump chamber with dialysate, opening a dialysate outlet valve of the dialysate input pump chamber, emptying the dialysate output pump chamber, opening a spent dialysate inlet valve, closing a spent dialysate outlet valve, and actuating the dialysate input pump to push fresh dialysate from the dialysate input pump chamber to the dialyser while simultaneously actuating the dialysate output pump to draw spent dialysate from the dialyser into the dialysate output pump chamber, and step (b) includes a second step (b2) comprising deactivating the blood pump, closing the blood return line, emptying the dialysate input pump chamber, filling the dialysate output pump chamber with spent dialysate, opening a dialysate inlet valve of the dialysate input pump, closing the dialysate outlet valve of the dialysate input pump, closing the spent dialysate inlet valve of the dialysate output pump, opening the spent dialysate outlet valve of the dialysate output pump, and activating the dialysate input pump flow fresh dialysate from a dialysate source into the dialysate input pump chamber while simultaneously activating the dialysate output pump to push spent dialysate to drain.

4. A method of operating a dialysis system including a blood side, a dialysate side containing a dialysate fluid circuit and a blood accumulator chamber, the dialysate fluid circuit comprising a dialysate input pump having a dialysate input pump chamber, and a dialysate output pump having a dialysate output pump chamber, a dialyser comprising a fluid chamber, a dialysate inlet, a dialysate outlet, a blood inlet, and a blood outlet, a blood circuit comprising a blood pump, the blood accumulator chamber, and a blood return line valve arranged on a blood return line downstream of the dialyser or at the blood outlet of the dialyser, and a blood filter arranged within the fluid chamber and dividing the dialysis system into the blood side and the dialysate side, the method comprising the steps of:

(a) connecting the vascular system of a patient to the blood circuit;

(b) supplying dialysate fluid to the dialysate fluid circuit and supplying blood from the vascular system of the patient to the blood circuit;

(c) creating a pressure differential across the blood filter via operation of at least one of the dialysate outlet pump and the blood pump, the pressure differential forcing blood plasma across the blood filter from the blood side onto the dialysate side and into the dialysate output pump chamber; and (d) deactivating the blood pump and operating the dialysate outlet pump to push blood plasma back across the blood filter into the blood side of the dialysis system.

5. The method of claim 4, wherein step (c) includes a first step (c1) comprising deactivating the blood pump, closing the blood return line to prevent flow of blood from the dialyser to the blood return line, filling the dialysate input pump chamber with dialysate, opening a dialysate outlet valve of the dialysate input pump chamber, emptying the dialysate output pump chamber, opening a spent dialysate inlet valve, closing a spent dialysate outlet valve, actuating the dialysate input pump to push fresh dialysate from the dialysate input pump chamber to the dialyser, while simultaneously actuating the dialysate output pump to draw spent dialysate from the dialyser into the dialysate output pump chamber, and step (c) includes a second step (c2) comprising deactivating the blood pump, closing the blood return line, emptying the dialysate input pump chamber, filling the dialysate output pump chamber with spent dialysate, opening a dialysate inlet valve of the dialysate input pump, closing dialysate outlet valve of the dialysate input pump, closing the spent dialysate inlet valve of the dialysate output pump, opening spent dialysate output valve of the dialysate output pump, and activating the dialysate input pump so as to flow fresh dialysate from a dialysate source into the dialysate input pump chamber while simultaneously activating the dialysate output pump to push spent dialysate to drain.

* * * * *